United States Patent
Koo et al.

(10) Patent No.: US 11,866,597 B2
(45) Date of Patent: Jan. 9, 2024

(54) 2-DIMENSIONAL MXENE SURFACE-MODIFIED WITH CATECHOL DERIVATIVE, METHOD FOR PREPARING THE SAME, AND MXENE ORGANIC INK INCLUDING THE SAME

(71) Applicant: KOREA INSTITUTE OF SCIENCE AND TECHNOLOGY, Seoul (KR)

(72) Inventors: Chong Min Koo, Seoul (KR); In Sik In, Chungju-si (KR); Tae Yun Ko, Seoul (KR); Daesin Kim, Seoul (KR); Se Hyun Doo, Seoul (KR); Seon Joon Kim, Seoul (KR); Soon Man Hong, Seoul (KR); Seung Sang Hwang, Seoul (KR); Kyung Youl Baek, Seoul (KR); Albert Lee, Seoul (KR); Sangho Cho, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 38 days.

(21) Appl. No.: 17/173,268

(22) Filed: Feb. 11, 2021

(65) Prior Publication Data
US 2021/0269664 A1  Sep. 2, 2021

(30) Foreign Application Priority Data

Feb. 13, 2020 (KR) .......................... 10-2020-0017337
Jan. 21, 2021 (KR) .......................... 10-2021-0008640

(51) Int. Cl.
*C09D 11/52* (2014.01)
*C09D 11/037* (2014.01)
(Continued)

(52) U.S. Cl.
CPC .............. *C09D 11/52* (2013.01); *C07C 47/565* (2013.01); *C07C 215/46* (2013.01); *C07F 7/28* (2013.01);
(Continued)

(58) Field of Classification Search
None
See application file for complete search history.

(56) References Cited

U.S. PATENT DOCUMENTS

2014/0162130 A1* 6/2014 Barsoum ............... C01B 32/914
                                                                429/231.8
2017/0088429 A1  3/2017 Shin et al.
(Continued)

FOREIGN PATENT DOCUMENTS

CN  103435829 A  * 12/2013
CN  103435829 A    12/2013
(Continued)

OTHER PUBLICATIONS

English machine translation of HU et al. (CN 103435829 A) accessed in PE2E Search; PDF pp. 1-8 is attached to the case file for reference. (Year: 2013).*
(Continued)

*Primary Examiner* — Katie L. Hammer
(74) *Attorney, Agent, or Firm* — Rabin & Berdo, P.C.

(57) ABSTRACT

The present disclosure relates to 2-dimensional MXenes surface-modified with catechol derivatives, a method for preparing the same, MXene organic ink including the same, and use thereof (e.g. flexible electrodes, conducive cohesive/adhesive materials, electromagnetic wave-shielding materials, flexible heaters, sensors, energy storage devices). Particularly, the simple, fast, and scalable surface-functionalization process of MXenes using catechol derivatives (e.g. ADOPA) organic ligands significantly
(Continued)

improves the dispersion stability in various organic solvents (including ethanol, isopropyl alcohol, acetone and acetonitrile) and produces highly concentrated organic liquid crystals of various MXenes (including $Ti_2CT_x$, $Nb_2CT_x$, $V_2CT_x$, $Mo_2CT_x$, $Ti_3C_2T_x$, $Ti_3CNT_x$, $Mo_2TiC_2T_x$, and $Mo_2Ti_2C_3T_x$). Such products offer excellent electrical conductivity, improved oxidation stability, excellent coating and adhesion abilities to various hydrophobic substrates, and composite processability with hydrophobic polymers. This finding will lead to further studies on the structures, properties, and physics of the organic MXene liquid crystals and their practical applications.

16 Claims, 17 Drawing Sheets

(51) Int. Cl.

| | |
|---|---|
| C09D 11/033 | (2014.01) |
| H01B 1/20 | (2006.01) |
| C07F 11/00 | (2006.01) |
| C07F 9/00 | (2006.01) |
| C07F 7/28 | (2006.01) |
| H01B 1/12 | (2006.01) |
| C09D 11/322 | (2014.01) |
| C09D 11/38 | (2014.01) |
| C07C 215/46 | (2006.01) |
| C07C 47/565 | (2006.01) |

(52) U.S. Cl.
CPC .............. *C07F 9/00* (2013.01); *C07F 11/00* (2013.01); *C09D 11/033* (2013.01); *C09D 11/037* (2013.01); *C09D 11/322* (2013.01); *C09D 11/38* (2013.01); *H01B 1/12* (2013.01); *H01B 1/20* (2013.01)

(56) References Cited

U.S. PATENT DOCUMENTS

| | | | | |
|---|---|---|---|---|
| 2017/0166756 | A1* | 6/2017 | Messersmith | ........... C23C 18/40 |
| 2017/0294546 | A1* | 10/2017 | Ghidiu | ................ C04B 35/5618 |
| 2019/0391099 | A1 | 12/2019 | Jung et al. | |
| 2020/0015391 | A1 | 1/2020 | Lee | |

FOREIGN PATENT DOCUMENTS

| | | |
|---|---|---|
| CN | 107001051 A | 8/2017 |
| CN | 108147464 A | 6/2018 |
| CN | 108190962 A | 6/2018 |
| CN | 108364802 A | 8/2018 |
| CN | 108389732 A | 8/2018 |
| CN | 109096754 A | 12/2018 |
| CN | 109417863 A | 3/2019 |
| CN | 110312766 A | 10/2019 |
| CN | 108147464 B | 12/2019 |
| CN | 110980711 A | 4/2020 |
| CN | 111595363 A | 8/2020 |
| CN | 112011067 A | 12/2020 |
| CN | 112111188 A | 12/2020 |
| EP | 2589578 A1 * | 5/2013 ............. B01J 13/02 |
| KR | 10-2017-0036507 A | 4/2017 |
| KR | 10-2017-0093041 A | 8/2017 |
| KR | 10-2019-0076341 A | 7/2019 |
| KR | 1020190090601 A | 8/2019 |
| KR | 10-2079728 B1 | 2/2020 |

OTHER PUBLICATIONS

Chuanfang (John) Zhang et al., "Stamping of Flexible, Coplanar Micro-Supercapacitors Using MXene Inks," Advanced Functional Materials, vol. 28, No. 1705506, pp. 1-10, Jan. 8, 2018.
Chuanfang John Zhang et al., "Oxidation Stability of Colloidal Two-Dimensional Titanium Carbides (MXenes)," Chemistry of Materials, vol. 29, pp. 4848-4856, May 9, 2017.
Daesin Kim et al., "Nonpolar Organic Dispersion of 2D Ti3C2Tx MXene Flakes via Simultaneous Interfacial Chemical Grafting and Phase Transfer Method," ACS Nano, vol. 13, pp. 13818-13828, Nov. 18, 2019.
Defu Gan et al., "Bioinspired functionalization of MXenes (Ti3C2Tx) with amino acids for efficient removal of heavy metal ions," Applied Surface Science, vol. 504, No. 144603, pp. 1-7, Nov. 5, 2019.
Jianmin Luo et al., "Pillared Structure Design of MXene with Ultralarge Interlayer Spacing for High-Performance Lithium-Ion Capacitors," ACS Nano, vol. 11, pp. 2459-2469, Dec. 21, 2016.
Kathleen Maleski et al., "Dispersions of Two-Dimensional Titanium Carbide MXene in Organic Solvents," Chemistry of Materials, vol. 29, No. 4, pp. 1632-1640, Feb. 17, 2017.
Michael Naguib et al., "Two-Dimensional Nanocrystals Produced by Exfoliation of Ti3AlC2," Advanced Materials, vol. 23, pp. 4248-4253, Aug. 22, 2011.
Korean Office Action in the counterpart Korean patent application No. 10-2021-0008640 dated Oct. 19, 2022.
Runmin Huang et al., "Self-assembled Ti3C2/MWCNTs nanocomposites modified glassy carbon electrode for electrochemical simultaneous detection of hydroquinone and catechol", Ecotoxicology and Environmental Safety, Sep. 4, 2019, pp. 1-8, vol. 184, No. 109619.
Extended European Search Report dated Aug. 6, 2021.
Heru Wang et al., Journal of Alloys and Compounds, "In situ polymerized Ti3C2Tx/PDA electrode with superior areal capacitance for supercapacitors", 2019. vol. 778, pp. 858-865.

* cited by examiner

AD-Ti$_3$C$_2$T$_x$ in Organic Solvents

Pristine Ti$_3$C$_2$T$_x$ in Organic Solvents

AD-MXene in Ethanol

Pristine MXene in Ethanol

DOPA-MXene  polyDOPA-MXene

2-DIMENSIONAL MXENE SURFACE-MODIFIED WITH CATECHOL DERIVATIVE, METHOD FOR PREPARING THE SAME, AND MXENE ORGANIC INK INCLUDING THE SAME

CROSS-REFERENCE TO RELATED APPLICATIONS

This application claims priority to Korean Patent Application No. 10-2020-0017337 filed on Feb. 13, 2020, Korean Patent Application No. 10-2021-0008640 filed on Jan. 21, 2021, and all the benefits accruing therefrom under 35 U.S.C. § 119, the contents of which in its entirety are herein incorporated by reference.

BACKGROUND

1. Field

The present disclosure relates to a 2-dimensional MXene surface-modified with a catechol derivative, a method for preparing the same, MXene organic ink including the same, and use thereof (e.g. flexible electrodes, conducive cohesive/adhesive materials, electromagnetic wave-shielding materials, flexible heaters, sensors, and energy storage devices).

Description of State-Supported Research and Development

The present disclosure is made under the support of construction technology research business of Ministry of Land, Infrastructure and Transport (Development of EMP Shielding Building Materials and Auxiliary Materials, Subject Reference No.: 1615010726), personal basic research business of Ministry of Science and ICT (Synthesis of Transition Metal Carbide MXene 2D Nanomaterials and Development of Electromagnetic Wave Shielding/Absorption/Control Technology Using The Same, Subject Reference No.: 1711084370), and future material discovery support business of Ministry of Science and ICT (Development of Source Technology for Multi-functional Composite Materials Based on 2-Dimensional Nanomaterials for Millimeter Wave Shielding/Absorption/Radiation, Subject Reference No.: 1711098073) with the supervision of Korea Institute of Science and Technology.

2. Background Art

MXene materials, which are transition metal carbides, transition metal nitrides, or transition metal carbonitrides, are a nanomaterial having a two-dimensional crystal structure, and have excellent properties, such as electrical conductivity, surface property controllability and solution processability, and thus its applicability to various industrial fields, including flexible electrodes, conductive cohesive/adhesive materials, electromagnetic wave-shielding materials, flexible heaters, sensors, energy storage electrodes and light-emitting diode displays, has been spotlighted.

In general, such MXenes having high electrical conductivity may be synthesized from a ceramic material called MAX. Particularly, MAX is a ternary layered-structure compound of a transition metal (titanium (Ti), niobium (Nb), vanadium (V), tantalum (Ta), molybdenum (Mo) or chromium (Cr)) represented by M, a Group 14 element (aluminum (Al) or silicon (Si)) represented by A, and carbon or nitrogen represented by X. In addition, MXenes are obtained by selectively removing ingredient A, such as aluminum, through an etching process using a strong acid, such as hydrofluoric acid (HF), from MAX to provide two-dimensional MXenes in which merely the transition metal and carbon (or nitrogen) remain. The surface of MXenes has terminal groups, such as —OH, =O, —F and —Cl, due to the synthetic path using a strong acid in an aqueous phase. Particularly, the MXenes have hydrophilicity through the —OH functional group of the terminal groups. The MXenes synthesized as mentioned above have excellent water dispersibility and may be applied to flexible electrodes, conductive cohesive/adhesive materials, electromagnetic wave-shielding materials, flexible heaters, sensors, energy storage electrodes, light emitting diode displays, or the like, through a solution process. Therefore, the MXenes are advantageous to formation of a film and coating having high electrical conductivity.

Although the MXenes obtained through a chemical etching process as mentioned above have an advantage in that it can be dispersed in water with ease by virtue of a large amount of functional groups, such as —OH (hydroxyl), =O (oxide), —F, —Cl, or the like, present on the surface thereof, the MXene dispersed in an aqueous phase is liable to oxidation, and particularly, it is easily oxidized by a water molecule itself and dissolved oxygen in water to be converted into a metal oxide and loses its electrical conductivity. In addition, the MXene merely capable of water dispersion through its surface hydrophilicity shows low binding force with the other hydrophobic materials (polymer, organic materials), thereby making it difficult to form a homogeneous composite with an organic single molecule or organic polymer undesirably. Further, there is a need for organic MXene ink dispersed in various organic solvents, besides water dispersion, in order to apply the MXene to film and coating solution processes, such as spray coating, spin coating and inkjet printing, favorable to the electronic industry.

SUMMARY

A technical problem to be solved by the present disclosure is to provide a chemically surface-modified two-dimensional MXene, which shows excellent dispersibility in various organic solvents, such as alcohols, through chemical modification of the surface of a two-dimensional MXene with catechol derivatives and has excellent electrical conductivity, solution processability and coatability, while providing improved oxidation stability.

Another technical problem to be solved by the present disclosure is to provide a method for surface modification of a two-dimensional MXene which shows a high processing yield within a short reaction time.

Still another technical problem to be solved by the present disclosure is to provide MXene organic ink which uses a surface-modified MXene having improved dispersibility in an organic solvent and has liquid crystal properties applicable to various industrial fields requiring alignment.

Yet another technical problem to be solved by the present disclosure is to provide MXene organic ink which has excellent electrical conductivity and coatability and can be applied to various industrial fields, such as flexible electrodes, conductive cohesive/adhesive materials, electromagnetic wave-shielding materials, flexible heaters, sensors, energy storage devices, light emitting diode displays, or the like.

In one general aspect, the present disclosure provides a two-dimensional MXene surface-modified chemically with a catechol derivative.

In another general aspect, the present disclosure provides a method for preparing a two-dimensional MXene surface-modified with a catechol derivative, including the steps of:
  (1) preparing an aqueous MXene solution including a two-dimensional MXene dispersed therein through an acid etching process; and
  (2) mixing and agitating the aqueous MXene solution obtained from step (1) with an organic solution including a catechol derivative dispersed in an organic solvent so that the two-dimensional MXene may be surface-modified with the catechol derivative.

In still another general aspect, the present disclosure provides MXene organic ink including a two-dimensional MXene surface-modified with a catechol derivative, wherein the surface-modified MXene is dispersed in an organic solvent.

According to an embodiment of the present disclosure, the two-dimensional MXene surface-modified with a catechol derivative can be dispersed stably in various organic solvents, particularly various alcohol type solvents at high concentration, and thus can be used for preparing high-concentration MXene organic ink having liquid crystal phases. In addition, the two-dimensional MXene surface-modified with a catechol derivative ensures oxidation stability, unlike its aqueous solution, and thus shows improved long-term stability, and allows introduction of an additional subsequent process with ease by controlling the compositions and lengths of various terminal functional groups substituted at the polyphenol moiety of the catechol derivative to provide various functionalities.

In addition, the two-dimensional MXene surface-modified with a catechol derivative according to an embodiment of the present disclosure and MXene organic ink including the same can form composites with various organic single molecules and organic polymers and can be applied to various industrial fields, such as flexible electrodes, conductive cohesive/adhesive materials, electromagnetic wave-shielding materials, flexible heaters, sensors, energy storage devices, light emitting diode displays, or the like, by virtue of excellent electrical conductivity and coatability.

DETAILED DESCRIPTION

Figure 1:
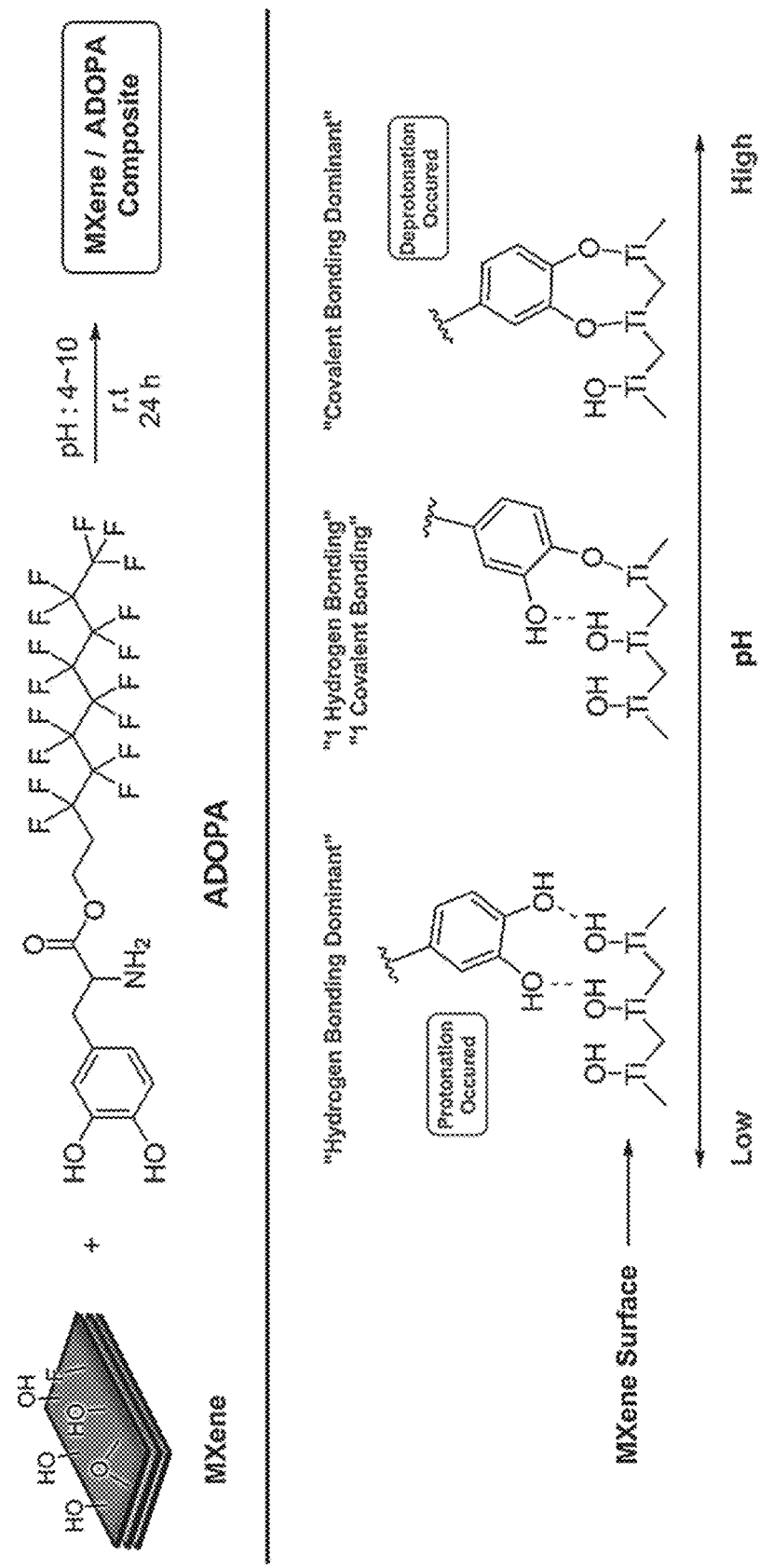
FIG. 1 and FIG. 2 are schematic views illustrating the method for preparing a surface-modified two-dimensional MXene according to an embodiment of the present disclosure.

Hereinafter, a detailed description of the present disclosure is given.

In one aspect of the present disclosure, there is provided a two-dimensional MXene surface-modified with a catechol derivative.

According to an embodiment, the catechol derivative may include a polyphenol moiety in the form of a phenyl group containing 2-5 hydroxyl (—OH) groups.

According to an embodiment, the catechol derivative may be a structure obtained by a chemical reaction between an organic substance containing the polyphenol moiety and various types of alcohol derivatives, and more particularly, may be represented by any one of the following Chemical Formula 1 to Chemical Formula 8. Herein, in the case of Chemical Formula 1, it represents a structure obtained by a chemical reaction between an example of catechol derivatives, i.e. 3,4-dihydroxyl-DL-phenylalanine (DOPA) and an alcohol derivative.

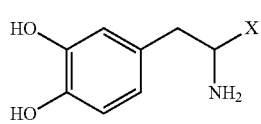

[Chemical Formula 1]

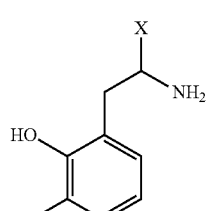

[Chemical Formula 2]

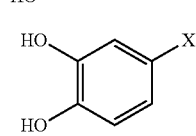

[Chemical Formula 3]

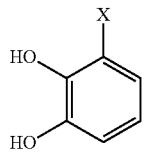

[Chemical Formula 4]

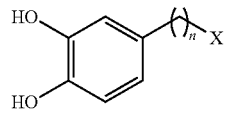

[Chemical Formula 5]

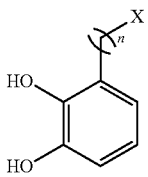

[Chemical Formula 6]

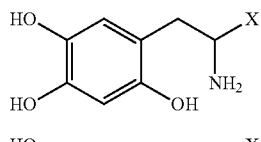

[Chemical Formula 7]

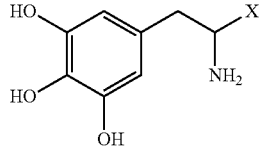

[Chemical Formula 8]

Herein, X may be selected from a hydrogen atom (—H), ester group (—COOR), amide group (—CONHR), thioester group (—COSR), hydrocarbon group (—R) and an ether group (—R—O—R'—), each of R and R' may be independently selected from C1-C25 aliphatic hydrocarbons and aromatic hydrocarbons, and n may be an integer of 1-10.

According to an embodiment, each of R and R' may independently represent a saturated or unsaturated cyclic or chain-like hydrocarbon selected from C1-C25 alkyl, C2-C24 alkenyl, C2-C25 alkynyl and C6-C25 aryl groups.

More particularly, each of R and R' may independently represent a saturated or unsaturated cyclic or chain-like hydrocarbon selected from C1-C13 alkyl, C2-C13 alkenyl, C2-C13 alkynyl and C6-C10 aryl groups, but is not limited thereto.

According to an embodiment, each of R and R' may independently represent a saturated or unsaturated heterocyclic hydrocarbon including 1-25 carbon atoms and at least one heteroatom selected from nitrogen, oxygen and sulfur.

According to an embodiment, the saturated or unsaturated chain-like hydrocarbon may include at least one selected from nitrogen, oxygen, sulfur, sulfinyl and sulfonyl in the middle of the chain or at a side chain of the chain, or not.

According to an embodiment, each of the cyclic or chain-like hydrocarbon and heterocyclic hydrocarbon may not be substituted or may be independently substituted with at least one substituent selected from a C1-C5 alkyl group, C6-C10 aryl group, fluorine, chlorine, bromine, and iodine.

According to an embodiment, the catechol derivative may be a compound represented by any one of the following Chemical Formula 9 to Chemical Formula 23, but is not limited thereto, wherein the number of carbon atoms forming each hydrocarbon group is not particularly limited, as long as the hydrocarbon group includes a polyphenol moiety at one side thereof and a hydrophobic functional group at the other side thereof so that it may be dispersed in an organic solvent.

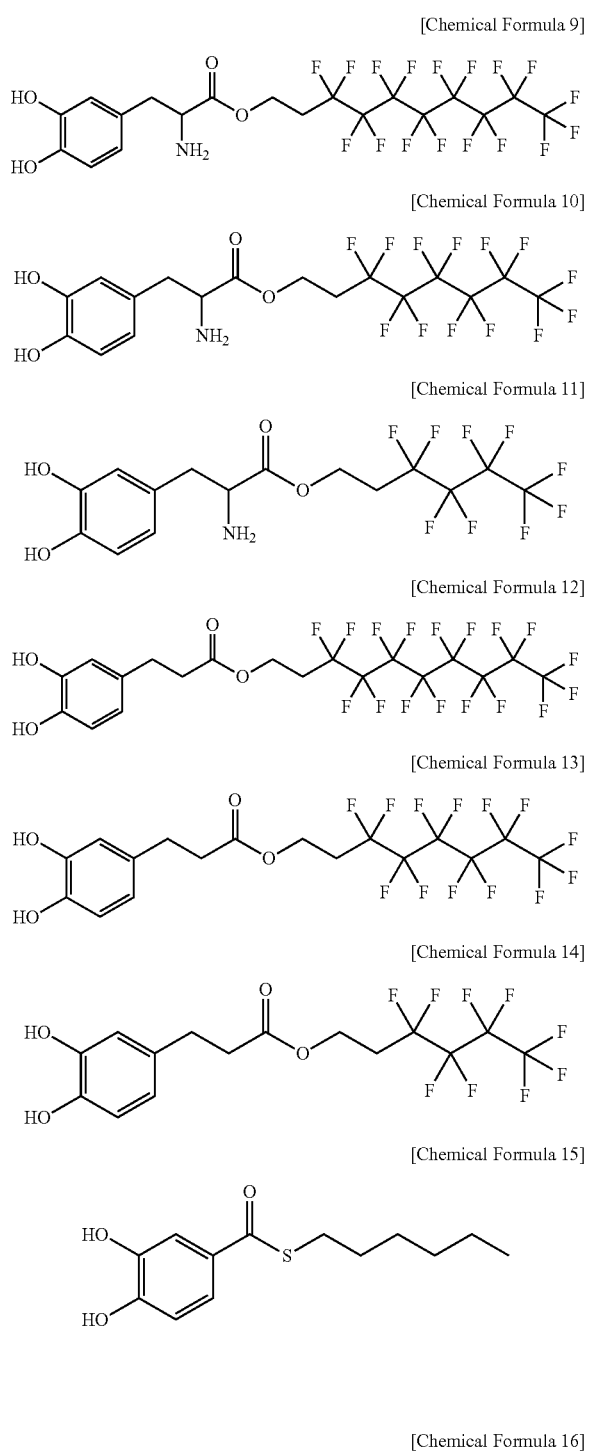

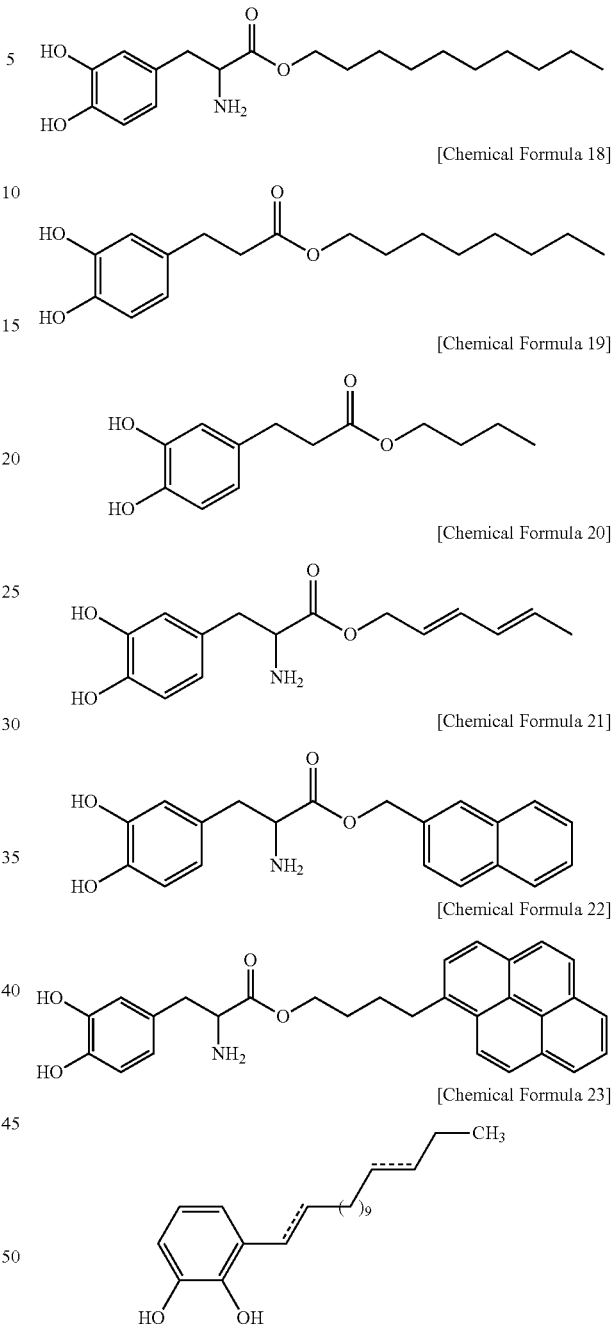

According to an embodiment, the catechol derivative may also include a polymer having a catechol derivative as a monomer. That is, the catechol derivative may include a poly-catechol derivative having a compound represented by any one of Chemical Formulas 1-8, more specifically, by any one of Chemical Formulas 9-23, as a monomer.

According to an embodiment, the two-dimensional MXene may include at least one layer with a two-dimensional array of crystal cells represented by the empirical formula of $M_{n+1}X_n$.

Herein, each X is positioned in an octahedral array formed of a plurality of M elements, wherein M is at least one metal selected from the group consisting of Group IIIB metals, Group IVB metals, Group VB metals, and Group VIB metals, each X represents C, N, or a combination thereof, and n may be 1, 2, 3, or 4.

According to an embodiment, particular examples of M may include Sc, Y, Lu, Ti, Zr, Hf, V, Nb, Ta, Cr, Mo, W, or a combination thereof, but are not limited thereto. In addition, particular examples of the empirical formula of $M_{n+1}X_n$ may include $Sc_2C$, $Ti_2C$, $Ti_3C_2$, $Nb_2C$, $V_2C$, $Ta_4C_3$, $Mo_2TiC_2$, $Mo_2Ti_2C_3$, $Cr_2TiC_2$, $Ti_2N$, $Ti_3CN$, $Mo_2C$, $Nb_4C_3$, $Zr_3C_2$, $Ti_4N_3$, $V_4C_3$, $Hf_3C_2$, $Mo_2N$, $Cr_2C$, $Zr_2C$, $Nb_2C$, $Hf_2C$, $V_3C_2$, $Ta_3C_2$, or $Ti_4C_3$, but are not limited thereto.

According to another embodiment, the two-dimensional MXene may include at least one layer with a two-dimensional array of crystal cells represented by the empirical formula of $M'_2M''_nX_{n+1}$.

Herein, each X is positioned in an octahedral array formed of a plurality of M' and M'' elements, wherein M' and M'' are different from each other, and each of M' and M'' is at least one metal selected from the group consisting of Group IIIB metals, Group IVB metals, Group VB metals, and Group VIB metals, each X represents C, N, or a combination thereof, and n may be 1 or 2.

According to another embodiment, particular examples of M' and M'' may include Ti, V, Nb, Ta, Cr, Mo or a combination thereof, but are not limited thereto. In addition, particular examples of the empirical formula of $M'_2M''_nX_n+_1$ may include $Mo_2VC_2$, $Mo_2TaC_2$, $Mo_2NbC_2$, $Cr_2VC_2$, $Cr_2TaC_2$, $Cr_2NbC_2$, $Ti_2TaC_2$, $Ti_2NbC_2$, $V_2TaC_2$, $V_2TiC_2$, $Mo_2V_2C_3$, $Mo_2Nb_2C_3$, $Mo_2Ta_2C_3$, $Cr_2Ti_2C_3$, $Cr_2Ta_2C_3$, $Cr_2V_2C_3$, $Cr_2Nb_2C_3$, $Nb_2Ta_2C_3$, $Ti_2Nb_2C_3$, $Ti_2Ta_2C_3$, $V_2Nb_2C_3$, $V_2Ta_2C_3$, or $V_2Ti_2C_3$, but are not limited thereto.

According to an embodiment, the two-dimensional MXene to be surface-modified may be a free-standing two-dimensional assembly of continuously independent crystal structures, or a stacked assembly in which the crystal structures are stacked. In the case of a stacked assembly, atoms, ions or molecules may be intercalated at least among several layers, wherein the intercalated atoms or ions may be lithium. Therefore, the surface-modified two-dimensional MXene according to an embodiment of the present disclosure may also be used for an energy storage device, such as a battery or supercapacitor.

Figure 3:
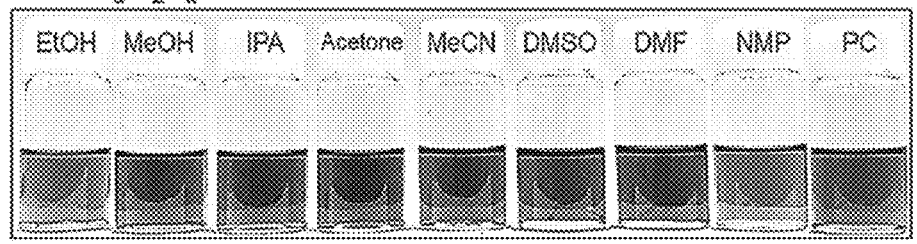
FIG. 3 shows the results of comparing a non-surface modified MXene with the surface-modified two-dimensional MXene according to an embodiment of the present disclosure in terms of dispersibility in various organic solvents.
Figure 3:
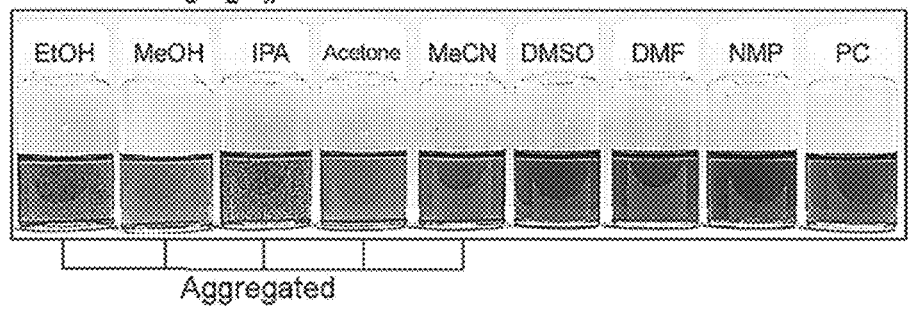

In addition, since the surface-modified two-dimensional MXene according to an embodiment of the present disclosure retains the crystal structure of a two-dimensional MXene before surface modification, as shown in FIG. 3, it has unique properties, such as excellent electrical conductivity, magnetic loss and dielectric loss characteristics, and thus can be used as a conductive flexible electrode, a heater or an electromagnetic wave-shielding material and -absorbing material.

In another aspect of the present disclosure, there is provided a method for preparing a two-dimensional MXene surface-modified with a catechol derivative.

According to an embodiment, the method for manufacturing a surface-modified two-dimensional MXene includes the steps of: (1) preparing an aqueous MXene solution including a two-dimensional MXene dispersed therein through an acid etching process; and (2) mixing and agitating the aqueous MXene solution obtained from step (1) with an organic solution including a catechol derivative dispersed in an organic solvent so that the two-dimensional MXene may be surface-modified with the catechol derivative.

In still another aspect of the present disclosure, there is provided a method for manufacturing MXene organic ink including the surface-modified two-dimensional MXene.

According to an embodiment of the present disclosure, the method for manufacturing MXene organic ink including the surface-modified two-dimensional MXene may further include a step of carrying out phase separation of the reaction product of the aqueous two-dimensional MXene solution and the organic solution of the catechol derivative obtained from steps (1) and (2), removing the aqueous layer, and controlling the concentration of the resultant organic solution including the surface-modified two-dimensional MXene dispersed therein, or substituting the organic solution with a desired organic solvent.

According to an embodiment, the etchant used in step (1) of acid etching may include an $F^-$-containing strong acid, such as HF, $NH_4HF_2$, or HCl—LiF mixture, but is not limited thereto. The MXene obtained through the acid etching step may be represented by the formula of $M_{n+1}X_n(T_x)$ or $M'_2M''_nX_{n+1}(T_x)$, wherein $T_x$ represents a terminal group formed on the surface of the two-dimensional MXene and includes —OH, =O, —F, or a combination thereof.

According to an embodiment, particular examples of the organic solvent may include alkanes, olefins, alcohols, aldehydes, amines, esters, ethers, ketones, aromatic hydrocarbons, hydrogenated hydrocarbons, terpene olefins, halogenated hydrocarbons, heterocyclic compounds, nitrogen-containing compounds, sulfur-containing compounds, or the like. For example, the organic solvent may be at least one selected from the group consisting of ethanol, methanol, isopropyl alcohol, n-hexanol, acetone, acetonitrile, dimethyl sulfoxide, dimethyl formamide, propylene carbonate, N-methyl-2-pyrrolidone and tetrahydrofuran, but is not limited thereto. Any organic solvent may be used, as long as it can disperse the catechol derivative as a surface-modifying agent for the two-dimensional MXene.

The organic solvent has a unique solubility parameter and shows high dispersibility, when a material to be dispersed or dissolved in the organic solvent has a solubility parameter similar to the solubility parameter of the organic solvent.

Therefore, it is possible to control dispersibility in an organic solvent by controlling the substituents, composition, length, etc. of the terminal group of a catechol derivative depending on the polarity of an organic solvent used for dispersion.

Herein, the agitation rate in step (2) may be selected suitably by those skilled in the art depending on the volume of a solution, agitator, presence of a magnetic bar, or the like. Simple hand shaking may be used, as long as it can cause an interfacial reaction.

In addition, according to an embodiment, the agitation in step (2) may be carried out at a temperature lower than the boiling point of the organic solvent used in the method. Preferably, the agitation in step (2) may be carried out at a temperature of 10-40° C. For example, the agitation in step (2) may be carried out at a temperature of 10° C. or more, 11° C. or more, 12° C. or more, 13° C. or more, 14° C. or more, 15° C. or more, 16° C. or more, 17° C. or more, 18° C. or more, 19° C. or more, 20° C. or more, 21° C. or more, 22° C. or more, 23° C. or more, 24° C. or more, 25° C. or more, 26° C. or more, 27° C. or more, 28° C. or more, 29° C. or more, 30° C. or more, 31° C. or more, 32° C. or more, 33° C. or more, 34° C. or more, 35° C. or more, 36° C. or more, 37° C. or more, 38° C. or more, or 39° C. or more, and 40° C. or less, 39° C. or less, 38° C. or less, 37° C. or less, 36° C. or less, 35° C. or less, 34° C. or less, 33° C. or less, 32° C. or less, 31° C. or less, 30° C. or less, 29° C. or less, 28° C. or less, 27° C. or less, 26° C. or less, 25° C. or less, 24° C. or less, 23° C. or less, 22° C. or less, 21° C. or less, 20° C. or less, 19° C. or less, 18° C. or less, 17° C. or less, 16° C. or less, 15° C. or less, 14° C. or less, 13° C. or less, 12° C. or less, or 11° C. or less.

According to an embodiment, the agitation in step (2) may be carried out for 1-48 hours. For example, the agitation in step (2) may be carried out for 1 hour or more, 3 hours or more, 5 hours or more, 7 hours or more, 9 hours or more, 12 hours or more, 15 hours or more, 18 hours or more, 20 hours or more, 22 hours or more, 23 hours or more, 24 hours or more, 25 hours or more, 26 hours or more, 27 hours or more, 29 hours or more, 32 hours or more, 34 hours or more, 36 hours or more, 38 hours or more, 40 hours or more, 42 hours or more, 44 hours or more, or 46 hours or more, and 48 hours or less, 46 hours or less, 44 hours or less, 42 hours or less, 40 hours or less, 38 hours or less, 36 hours or less, 33 hours or less, 30 hours or less, 28 hours or less, 26 hours or less, 25 hours or less, 24 hours or less, 23 hours or less, 22 hours or less, 20 hours or less, 17 hours or less, 13 hours or less, 10 hours or less, 8 hours or less, 6 hours or less, or 4 hours or less.

Figure 2:
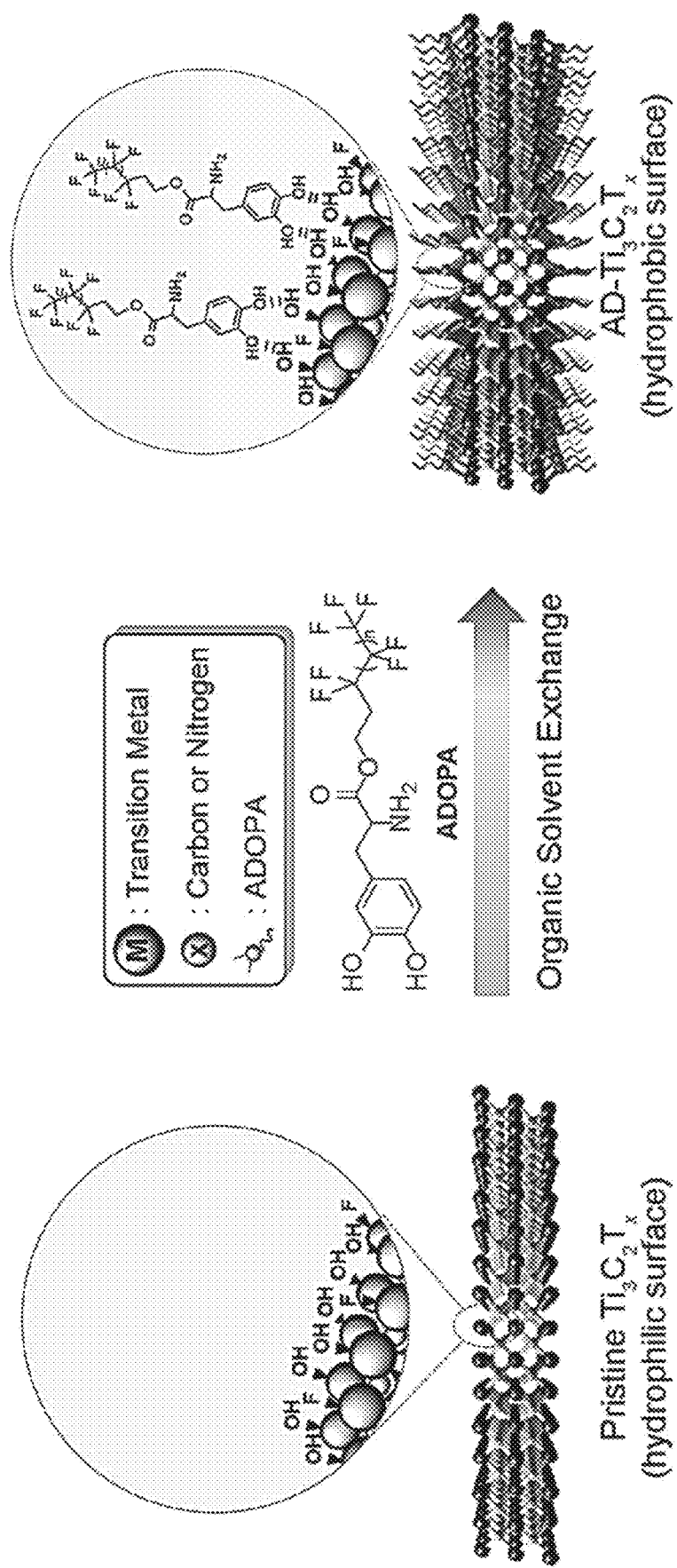

As shown in FIG. 1 and FIG. 2, when mixing and agitating a two-dimensional MXene with a catechol derivative (ADOPA; AD), the catechol derivative is adsorbed homogeneously on the surface of MXene through hydrogen bonding, covalent bonding, or the like, and thus a surface-modified two-dimensional MXene may be obtained.

In addition, the aqueous MXene solution obtained from step (1) may be controlled in its pH to provide an acidic solution with a pH of 1-6, neutral solution with a pH of 6-7 and a basic solution with a pH of 8-14. When carrying out the surface modification of step (2), hydrogen bonding is predominant under a low pH condition, and covalent bonding is predominant under a high pH condition, as shown in FIG. 1. In this manner, it is possible to carry out a reaction in a wide pH range.

According to an embodiment, the organic solution in step (3) may be concentrated through natural evaporation, rotary vacuum evaporation, centrifugal separation, etc., or may be diluted by adding a solvent thereto. In addition, the substitution with an organic solvent may be carried out by using centrifugal separation, sequential concentration and dilution, dialysis, or the like.

In still another aspect of the present disclosure, there is provided MXene organic ink including the two-dimensional MXene surface-modified with a catechol derivative, wherein the surface-modified two-dimensional MXene is dispersed in an organic solvent.

The obtained two-dimensional MXene surface-modified with a catechol derivative or MXene organic ink shows significantly improved oxidation stability as compared to a conventional aqueous MXene solution to provide significantly improved long-term storage stability, and can be used more efficiently for various solution coating processes, such as spray coating, spin coating, ink jet printing, or the like. In addition, since the surface-modified two-dimensional MXene has high dispersibility, it is possible to obtain high-concentration MXene organic ink. Further, the high-concentration MXene organic ink may be applied to production of various materials, such as highly aligned electrodes, polymer composites, self-assembled fibers and films, by virtue of its liquid crystal phase properties. Further, it is possible to obtain various composites with various hydrophobic organic single molecules or organic polymer materials advantageously, and to realize high industrial applicability to production of high-conductivity films and coating applicable to flexible electrodes, conductive cohesive/adhesive materials, electromagnetic wave-shielding materials, flexible heaters, sensors, energy storage electrodes, light emitting diode displays, or the like.

For example, it is possible to obtain a film formed on a substrate with a uniform thickness by applying the MXene organic ink including the surface-modified two-dimensional MXene according to an embodiment of the present disclosure uniformly onto a substrate, and allowing the solvent to evaporate.

According to another embodiment, the MXene organic ink may include any particles and/or polymers other than the surface-modified two-dimensional MXene.

Particular examples of the particles may include, but are not limited to: metals, such as Ag, Au, Cu, Pd and Pt; metal oxides, such as $SiO_2$ and ITO; nitrides; carbides; semiconductors, including Si, GaAS and InP; glass, such as silica or boron-based glass; liquid crystals, such as poly(3,4-ethylenedioxythiophene); organic/inorganic porous bodies; and organic polymers.

Particular examples of the polymers include, but are not limited to: epoxy resin, polyvinyl chloride (PVC), polypropylene (PP), polyethylene (PE), polyetherimide (PEI), acrylate resin, polyamide (PA), acrylonitrile-butadiene-styrene resin (ABS), polyamideimide (PAI), polybenzoimidazole (PBI), polyphenylene sulfide (PPS), polytetrafluoroethylene (PTFE), polyvinylidene fluoride (PVDF), polyethylene terephthalate (PET), polyoxymethylene (POM), polyether ketone (PEK), polyetherether ketone (PEEK), polyaryl etherketone (PAEK), liquid crystal polymer (LCP), polyimide (PI), polycarbonate (PC), self-reinforced polyphenylene (SPR), (meth)acrylate polymer, urethane (meth)acrylate polymer, polystyrene (PS), polyurethane and polysiloxane.

In the case of the MXene organic ink according to an embodiment of the present disclosure, it uses an organic solvent, and thus may be used for manufacturing a functional film including the two-dimensional MXene particles and having the unique properties thereof through a liquid phase process, such as spray coating, spin coating, ink jet printing or filtering, while the MXene is in a stabilized state by inhibiting oxidation effectively.

According to an embodiment, the MXene organic ink may include the surface-modified two-dimensional MXene dispersed in the organic solvent at a concentration of 1-100 mg/mL. More particularly, the MXene organic ink may include the surface-modified two-dimensional MXene dispersed in the organic solvent at a concentration of 1 mg/mL or more, 3 mg/mL or more, 5 mg/mL or more, 7 mg/mL or more, 10 mg/mL or more, 15 mg/mL or more, 20 mg/mL or more, 30 mg/mL or more, 40 mg/mL or more, 50 mg/mL or more, 60 mg/mL or more, 70 mg/mL or more, 80 mg/mL or more, or 90 mg/mL or more. On the other hand, the MXene organic ink may include the surface-modified two-dimensional MXene dispersed in the organic solvent at a concentration of 100 mg/mL or less, 90 mg/mL or less, 80 mg/mL or less, 70 mg/mL or less, 60 mg/mL or less, 50 mg/mL or less, 40 mg/mL or less, 30 mg/mL or less, 20 mg/mL or less, 15 mg/mL or less, or 10 mg/mL or less.

According to an embodiment, the MXene organic ink may have liquid crystal properties, when the concentration of the surface-modified two-dimensional MXene is 20 mg/mL or more, 30 mg/mL or more, 40 mg/mL or more, or 50 mg/mL or more.

In still another aspect of the present disclosure, there is provided a film including the MXene organic ink.

According to an embodiment, the film may be obtained through various solution coating processes, such as spray coating, spin coating, ink jet printing, filtering, multilayer coating or dip coating, using the MXene organic ink.

According to an embodiment, the coating or film including the surface-modified two-dimensional MXene, or the MXene organic ink including the surface-modified two-dimensional MXene may have an electrical conductivity of at least 1 S/cm, particularly at least 100 S/cm, 500 S/cm, 1,000 S/cm, 1,500 S/cm, 2,000 S/cm, 2,500 S/cm, preferably at least 3,000 S/cm, more preferably at least 3,300 S/cm. In addition, the coating or film may have a surface conductivity of at most 8,000 S/cm, 9,000 S/cm, preferably 10,000 S/cm, more preferably 20,000 S/cm.

According to an embodiment, the coating may have a thickness of 1-999 nm. For example, the coating may have a thickness of 1 nm or more, 5 nm or more, 10 nm or more, 50 nm or more, 100 nm or more, 150 nm or more, 200 nm or more, 250 nm or more, 300 nm or more, 350 nm or more, 400 nm or more, 450 nm or more, 500 nm or more, 550 nm or more, 600 nm or more, 700 nm or more, or 800 nm or more. In addition, the coating may have a thickness of 999 nm or less, 950 nm or less, 900 nm or less, 800 nm or less, 700 nm or less, 600 nm or less, 550 nm or less, 500 nm or less, 450 nm or less, 400 nm or less, 350 nm or less, 300 nm or less, 250 nm or less, 200 nm or less, 150 nm or less, 100 nm or less, or 50 nm or less.

According to an embodiment, the film may have a thickness of 1-500 μm. For example, the film may have a thickness of 1 μm or more, 2 μm or more, 3 μm or more, 4 μm or more, 5 μm or more, 6 μm or more, 7 μm or more, 7.5 μm or more, 8 μm or more, 9 μm or more, 10 μm or more, 10.5 μm or more, 11 μm or more, 12 μm or more, 12.5 μm or more, 13 μm or more, 14 μm or more, 15 μm or more, 20 μm or more, 30 μm or more, 40 μm or more, 50 μm or more, 100 μm or more, 150 μm or more, 200 μm or more, 250 μm or more, 300 μm or more, 350 μm or more, 400 μm or more, or 450 μm or more. In addition, the film may have a thickness of 500 μm or less, 470 μm or less, 420 μm or less, 370 μm or less, 320 μm or less, 270 μm or less, 230 μm or less, 170 μm or less, 120 μm or less, 60 μm or less, 50 μm or less, 40 μm or less, 30 μm or less, 20 μm or less, 20 μm or less, 15 μm or less, 14 μm or less, 13 μm or less, 12 μm or less, 11.5 μm or less, 11 μm or less, 10.5 μm or less, 10 μm or less, 9 μm or less, 8.5 μm or less, 8 μm or less, 7 μm or less, 6 μm or less, 5 μm or less, 4 μm or less, 3 μm or less, or 2 μm or less.

In still another aspect of the present disclosure, there is provided an electrically conductive flexible electrode, an electrically conductive polymer composite, or an electromagnetic wave-shielding composite, including the MXene organic ink.

The surface-modified two-dimensional MXene is favorable to formation of composites with various hydrophobic organic single molecules or organic polymer materials. Therefore, the surface-modified two-dimensional MXene may be applied to flexible electrodes, conductive cohesive/adhesive materials, electromagnetic wave-shielding materials, flexible heaters, sensors, energy storage electrodes, light emitting diode displays, or the like.

According to an embodiment, the electrically conductive polymer composite and electromagnetic wave-shielding composite may further include any particles and/or polymers other than the MXene organic ink. Particular examples of the particles and polymers are the same as described above.

Hereinafter, the present disclosure will be explained in more detail with reference to examples and test examples. However, the following examples and test examples are for illustrative purposes only, and the scope of the present disclosure should not be construed as limited to the exemplary embodiments set forth therein. In addition, various modifications, substitutions and insertions generally known to those skilled in the art may be made to the present disclosure, and such modifications, substitutions and insertions also fall within the scope of the present disclosure.

Preparation Example 1: Surface Modification of Two-Dimensional MXene Using Catechol Derivative and Preparation of MXene Organic Ink; Comparative Examples 1-8 and Examples 1-25

First, an aqueous solution (Comparative Example 1) of exfoliated MXene ($Ti_3C_2T_x$) prepared by treating $Ti_3AlC_2$ powder (average particle diameter≤40 μm) with LiF (available from Alfa Aesar, 98.5%)-HCl (available from DAEJUNG, 35-37%) was diluted to 1 mg/mL to prepare 35 mL of a dilution. Next, 3.5 mg of each of the catechol derivatives represented by Chemical Formula 9 to Chemical Formula 23 (Examples 1-15, respectively) was dissolved in 10 mL of each of the organic solvents (ethanol, methanol, isopropyl alcohol, n-hexanol, acetone, acetonitrile, dimethyl sulfoxide, dimethyl formamide, propylene carbonate, N-methyl-2-pyrrolidone, and tetrahydrofuran) (available from DAESUNG) to prepare organic solutions. The aqueous MXene solution according to Comparative Example 1 was mixed with each of the organic solutions, and each mixed solution was agitated at room temperature for 24 hours to carry out reaction. After 24 hours, agitation was stopped and centrifugal separation was carried out to separate MXene surface-modified with a catechol derivative. Then, the surface-modified MXene was washed three to five times with an organic solvent to be substituted (ethanol, methanol, isopropyl alcohol, n-hexanol, acetone, acetonitrile, dimethyl sulfoxide, dimethyl formamide, propylene carbonate, N-methyl-2-pyrrolidone and tetrahydrofuran) (available from DAESUNG) to obtain MXene organic ink.

In addition, Comparative Examples 2-8 were obtained in the same manner as Comparative Example 1, and Examples 16-25 were obtained in the same manner as Examples 1-15, except that $M_{n+1}AlX_n$ powder and catechol derivatives were used according to the following Table 1.

TABLE 1

|  | $M_{n+1}AlX_n$ Powder | Catechol derivative |
|---|---|---|
| Comp. Ex. 2 | $Ti_3AlCN$ | — |
| Comp. Ex. 3 | $Ti_2AlC$ | — |
| Comp. Ex. 4 | $Mo_2Ti_2AlC_3$ | — |
| Comp. Ex. 5 | $Nb_2AlC$ | — |
| Comp. Ex. 6 | $V_2AlC$ | — |
| Comp. Ex. 7 | $Mo_2AlC$ | — |
| Comp. Ex. 8 | $Mo_2TiAlC_2$ | — |
| Ex. 16 | $Ti_3AlCN$ | Chemical Formula 9 |
| Ex. 17 | $Ti_3AlCN$ | Chemical Formula 17 |
| Ex. 18 | $Ti_2AlC$ | Chemical Formula 9 |
| Ex. 19 | $Ti_2AlC$ | Chemical Formula 17 |
| Ex. 20 | $Mo_2Ti_2AlC_3$ | Chemical Formula 9 |
| Ex. 21 | $Mo_2Ti_2AlC_3$ | Chemical Formula 17 |
| Ex. 22 | $Nb_2AlC$ | Chemical Formula 9 |
| Ex. 23 | $V_2AlC$ | Chemical Formula 9 |
| Ex. 24 | $Mo_2AlC$ | Chemical Formula 9 |
| Ex. 25 | $Mo_2TiAlC_2$ | Chemical Formula 9 |

The appearance of the MXene organic ink including each of the surface-modified MXene (AD-$Ti_3C_2T_x$) according to Example 1 and non-surface modified MXene (pristine, $Ti_3C_2T_x$), according to Comparative Example 1 dispersed in each of ethanol (EtOH), methanol (MeOH), isopropyl alcohol (IPA), acetone, acetonitrile (MeCN), dimethyl sulfoxide (DMSO), dimethyl formamide (DMF), N-methyl-2-pyrrolidone (NMP) and propylene carbonate (PC) is shown in FIG. 3.

As shown in FIG. 3, the hydrophobically surface-modified MXene according to Example 1 shows a color of a typical green solution formed when well-dispersed MXene in each of various organic solvents is converted into a diluted concentration, while the non-surface modified MXene according to Comparative Example 1 causes aggregation of MXene particles, not dispersion of MXene particles, when being dispersed in ethanol, methanol, isopropyl alcohol, acetone or acetonitrile.

In addition, the appearance of MXene organic ink including each of the MXene according to Example 1 (AD-$Ti_3C_2T_x$), Example 16 (AD-$Ti_3CNT_x$), Example 18 (AD-$Ti_2CT_x$), Example 20 (AD-$Mo_2Ti_2C_3T_x$), Example 22 (AD-$Nb_2CT_x$), Example 23 (AD-$V_2CT_x$), Example 24 (AD-$Mo_2CT_x$), Example 25 (AD-$Mo_2TiC_2T_x$) and Comparative Examples 1-8 (Pristine-$Ti_3C_2T_x$; $Ti_3CNT_x$; $Ti_2CT_x$; $Mo_2Ti_2C_3T_x$; $Nb_2CT_x$; $V_2CT_x$; $Mo_2CT_x$; $Mo_2TiC_2T_x$), dispersed in ethanol, is shown in FIG. 4.

Figure 4:
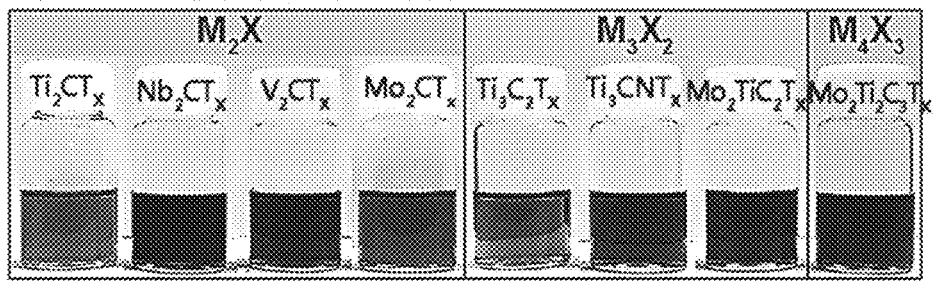
FIG. 4 shows the results of comparing a non-surface modified MXene with the surface-modified two-dimensional MXene according to an embodiment of the present disclosure in terms of dispersibility in ethanol.
Figure 4:
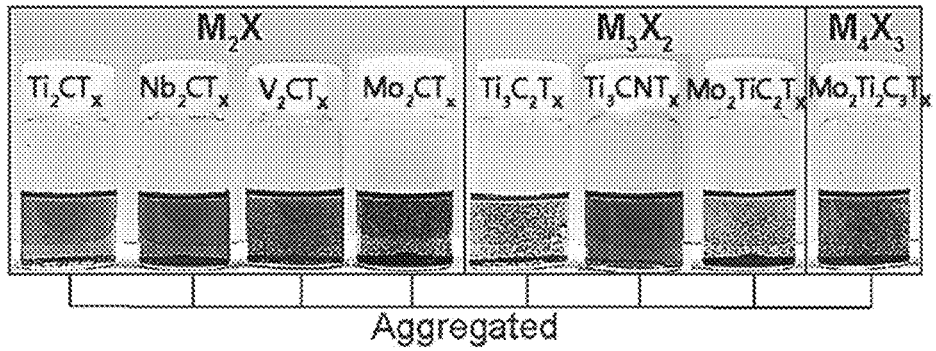

It can be seen from the results of FIG. 4 that when dispersing each surface-modified MXene according to Examples 1, 16, 18, 20 and 22-25 in ethanol, a unique color of each metal appears by virtue of high dispersibility, while the non-surface modified MXene according to each of Comparative Examples 1-8 is not dispersed in ethanol but the particles aggregate with one another.

Test Example 1: Determination of Electrical Conductivity of Surface-Modified Two-Dimensional MXene Organic Ink 1-1. The electrical conductivity of each MXene ($Ti_3C_2T_x$) organic ink according to Examples 1-15 was determined by using a 4-pin probe (MCP-TP06P PSP) equipped with Loresta GP meter (MCP-T610 model, available from MITSUIBISHI CHEMICAL). The results are shown in the following Table 2.

TABLE 2

| | Catechol derivative used for surface modification | Electrical conductivity (S/cm) |
|---|---|---|
| Ex. 1 | | 3,333 |
| Ex. 2 | | 3,157 |
| Ex. 3 | | 3,222 |
| Ex. 4 | | 2,994 |
| Ex. 5 | | 3,094 |
| Ex. 6 | | 3,157 |

TABLE 2-continued
| | Catechol derivative used for surface modification | Electrical conductivity (S/cm) |
|---|---|---|
| Ex. 7 | 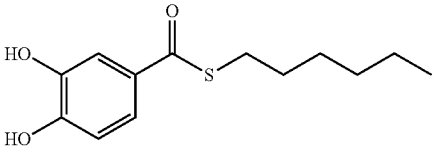 [SMILES: CCCCCCSC(=O)c1ccc(O)c(O)c1] | 2,891 |
| Ex. 8 | 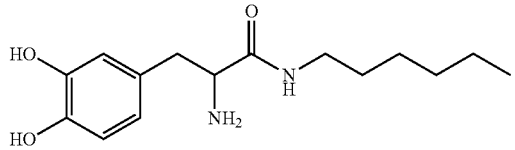 [SMILES: CCCCCCNC(=O)C(N)Cc1ccc(O)c(O)c1] | 3,267 |
| Ex. 9 | 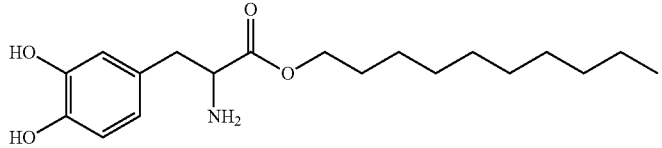 [SMILES: CCCCCCCCCCOC(=O)C(N)Cc1ccc(O)c(O)c1] | 2,983 |
| Ex. 10 | 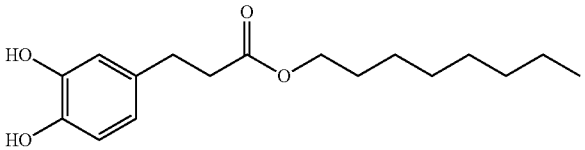 [SMILES: CCCCCCCCOC(=O)CCc1ccc(O)c(O)c1] | 3,121 |
| Ex. 11 | 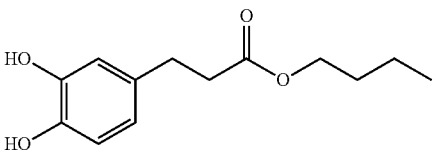 [SMILES: CCCCOC(=O)CCc1ccc(O)c(O)c1] | 3,201 |
| Ex. 12 | 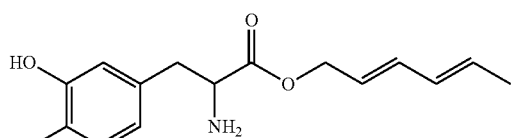 | 2,961 |
| Ex. 13 | 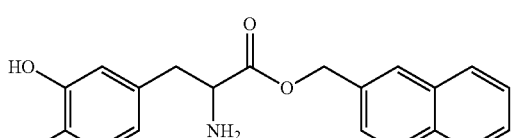 | 2,815 |
| Ex. 14 | 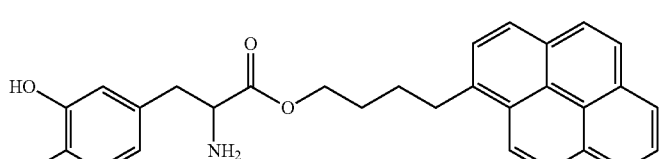 | 3,088 |
| Ex. 15 | 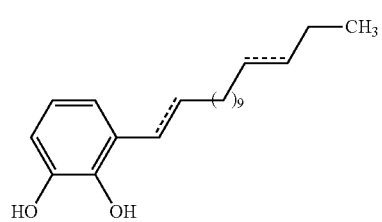 | 2,870 |

It can be seen from the results of Table 2 that the two-dimensional MXene surface-modified with a catechol derivative according to the present disclosure shows an electrical conductivity of at least 2,800 S/cm, and thus has electrical conductivity characteristics unique to the two-dimensional MXene before surface modification.

1-2. The electrical conductivity of each MXene (Examples 16 and 17: $Ti_3CNT_x$, Examples 18 and 19: $Ti_2CT_x$, Examples 20 and 21: $Mo_2Ti_2C_3T_x$) was determined by using a 4-pin probe (MCP-TP06P PSP) equipped with Loresta GP meter (MCP-T610 model, available from MITSUIBISHI CHEMICAL). The results are shown in the following Table 3.

Test Example 2: Analysis of Microstructure of Two-Dimensional MXene after Surface Modification Using SEM and TEM A scanning electron microscope (SEM) (Hitachi S4700, available from Hitachi) and transmission electron microscope (TEM) (alos F200X, available from FEI) were used to analyze the microstructure of the two-dimensional MXene surface-modified according to Example 1 and dispersed in ethanol, and that of the film obtained by using the same. In the case of the film, it was obtained through a vacuum filtration method using an anodic aluminum oxide film (pore size: 200 μm) of the two-dimensional MXene surface-

TABLE 3

| | Catechol derivative used for surface modification | Electrical conductivity (S/cm) |
|---|---|---|
| Ex. 16 | [structure] | 721 |
| Ex. 17 | [structure] | 688 |
| Ex. 18 | [structure] | 2,212 |
| Ex. 19 | [structure] | 1,999 |
| Ex. 20 | [structure] | 148 |
| Ex. 21 | [structure] | 139 |

Figure 5:
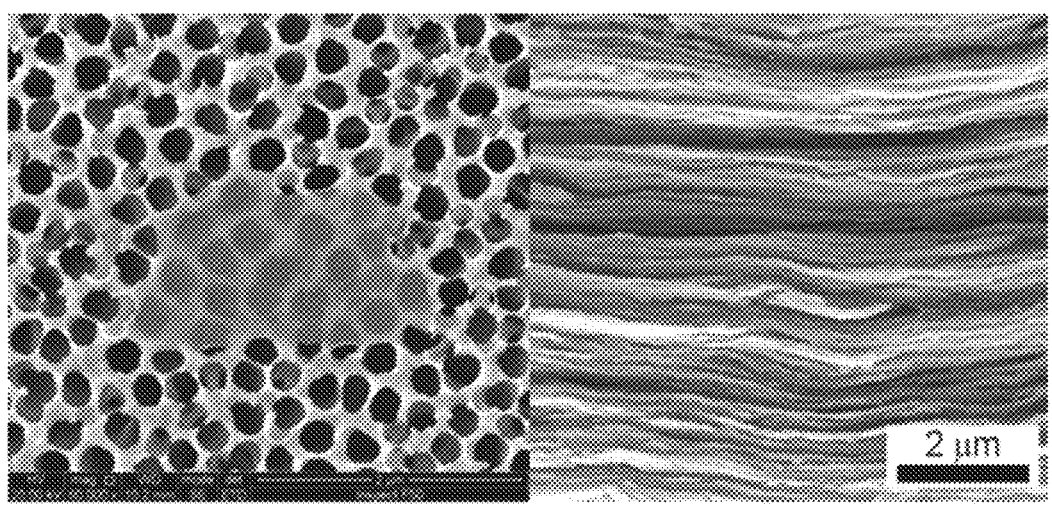
FIG. 5 shows the microstructure of the surface-modified two-dimensional MXene according to an embodiment of the present disclosure.
Figure 6:
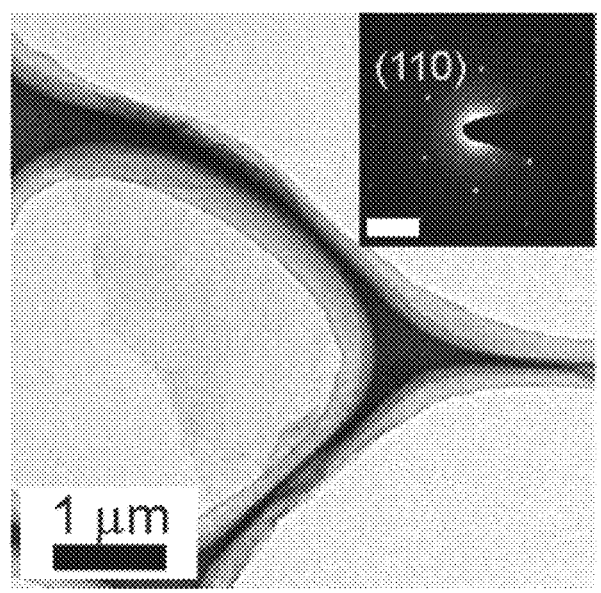
FIG. 6 illustrates single MXene sheets of the surface-modified two-dimensional MXene according to an embodiment of the present disclosure, as observed through a transmission electron microscope (TEM).

It can be seen from the results of Table 3 that various types of MXene, besides $Ti_3C_2T_x$, retain electrical conductivity characteristics unique to the two-dimensional MXene, when being surface-modified with a catechol derivative.

modified according to Example 1 and dispersed in ethanol. The results are shown in FIG. 5 and FIG. 6. As shown in FIG. 5 and FIG. 6, the film retains a single layer like the two-dimensional flake structure, even after surface modification (left side of FIG. 5; and FIG. 6). It can be seen that when a bulk film is obtained by using the surface-modified MXene solution dispersed in an organic solvent, the sheets of MXene are stacked well (right side of FIG. 5). It can be predicted from the above results that the two-dimensional MXene particles retain their unique properties even after surface modification.

Test Example 3: Gravimetric Analysis of Two-Dimensional MXene Using TGA after Surface Modification The two-dimensional MXene after surface modification was analyzed in terms of interlayer distance by using a thermogravimetric analyzer (TGA) (Q50, available from TA Instruments).

Figure 7:
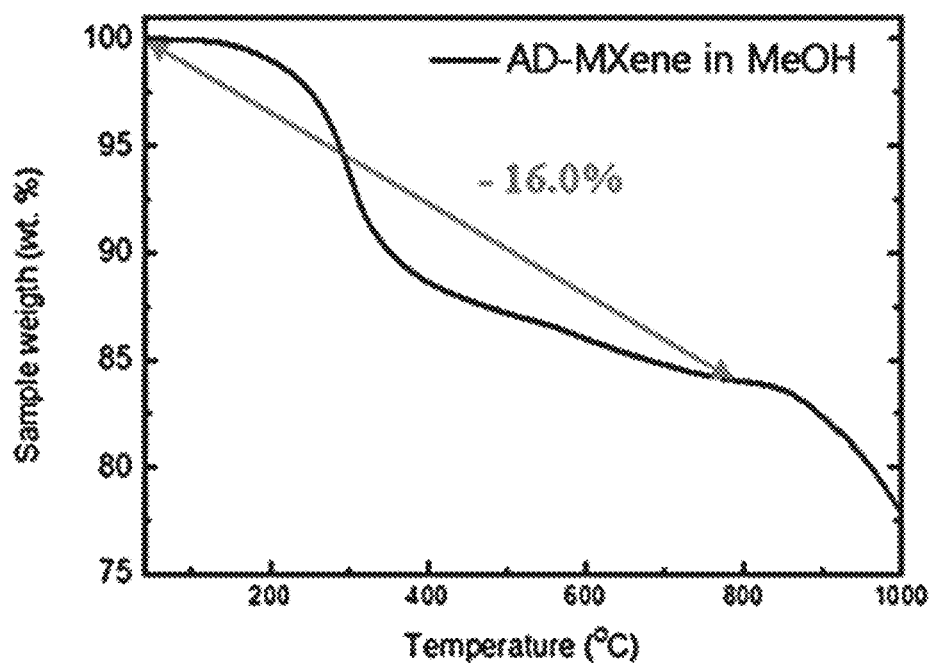
FIG. 7 and FIG. 8 are graphs illustrating the results of gravimetric analysis of the surface-modified two-dimensional MXene according to an embodiment of the present disclosure, before and after surface-modification.
Figure 7:
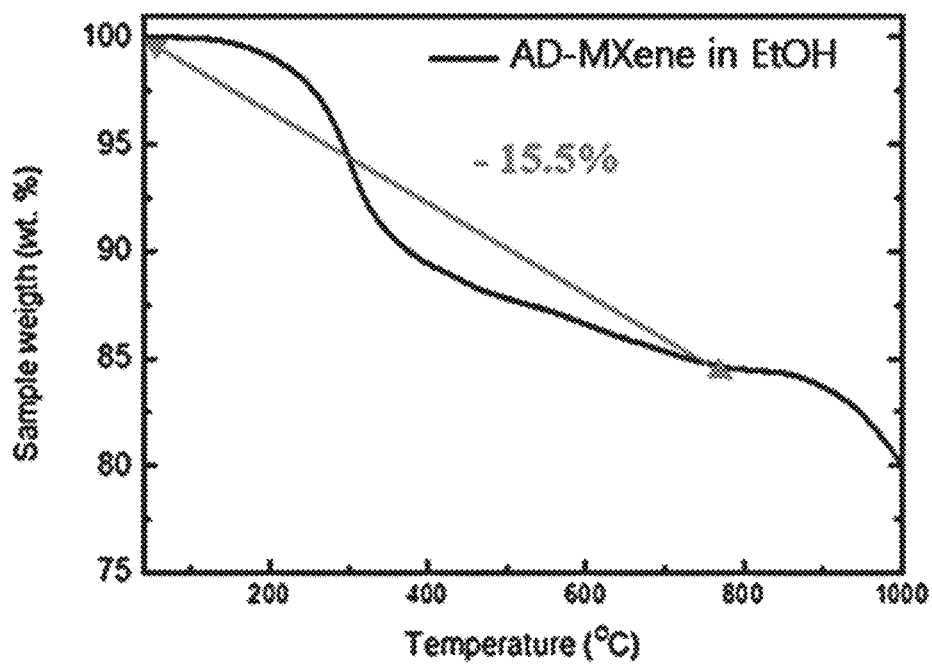

3-1. The two-dimensional MXene surface modified according to Example 1 and dispersed in each of methanol (upper side of FIG. 7) and ethanol (bottom side of FIG. 7) was subjected to gravimetric analysis. The results are shown in FIG. 7. As shown in FIG. 7, each surface-modified MXene shows a decrease in weight of about 16% and 15.5%, as compared to the MXene before surface modification. This suggests that the surface of the two-dimensional MXene is satisfactorily modified with a catechol derivative.

Figure 8:
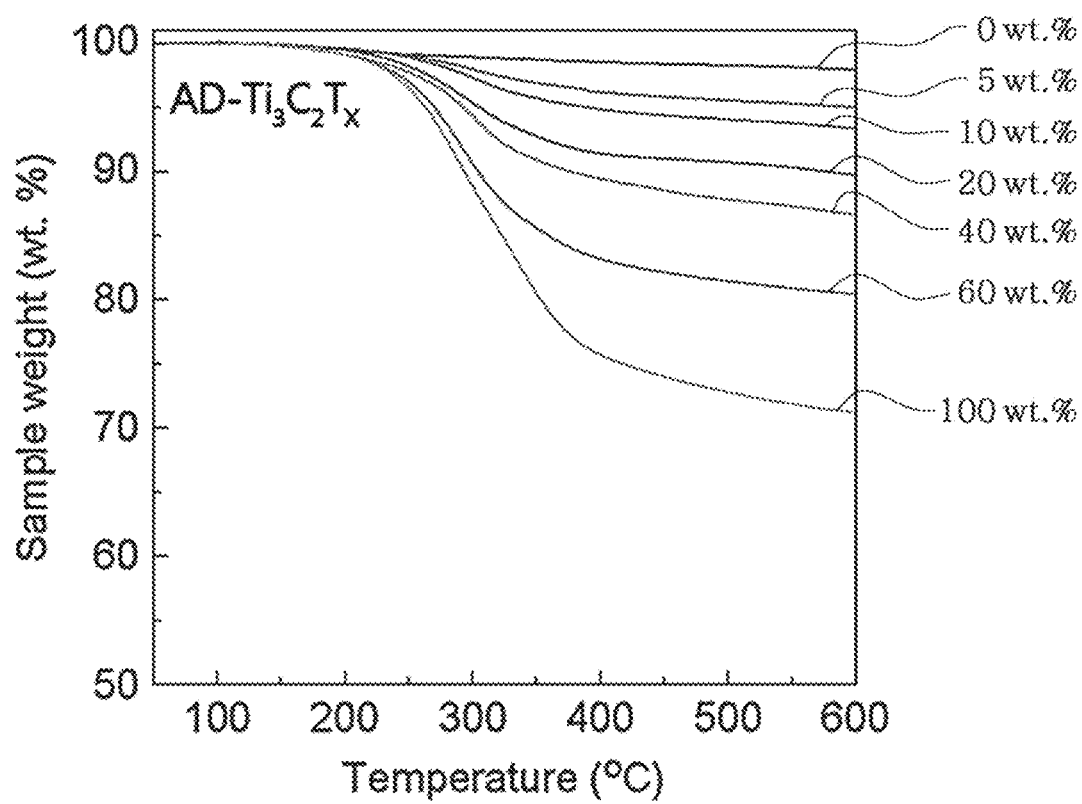

3-2. The two-dimensional MXene surface modified in the same manner as Example 1, except that a different content (5 wt %, 10 wt %, 20 wt %, 40 wt %, 60 wt % and 100 wt %) of a catechol derivative based on the weight of MXene was used to carry out reaction (surface modification), and dispersed in ethanol was subjected to gravimetric analysis. The results are shown in FIG. 8. As shown in FIG. 8, the surface-modified MXene shows a larger decrease in weight, as compared to the MXene before surface modification, gradually in proportion to the content of the catechol derivative. This suggests that the surface of the two-dimensional MXene is satisfactorily modified with a catechol derivative.

Test Example 4: Analysis of Interlayer Distance of Two-Dimensional MXene after Surface Modification Using XRD The two-dimensional MXene after surface modification was analyzed in terms of interlayer distance by using X-ray diffractometry (XRD) (D8 Discover, available from Bruker). Herein, the two-dimensional MXene surface modified in the same manner as Example 1, except that a different content (5 wt %, 10 wt %, 20 wt %, 40 wt %, 60 wt % and 100 wt %) of a catechol derivative based on the weight of MXene was used to carry out reaction (surface modification), and dispersed in ethanol was used as the surface-modified two-dimensional MXene to be analyzed. The results are shown in FIG. 9.

Figure 9:
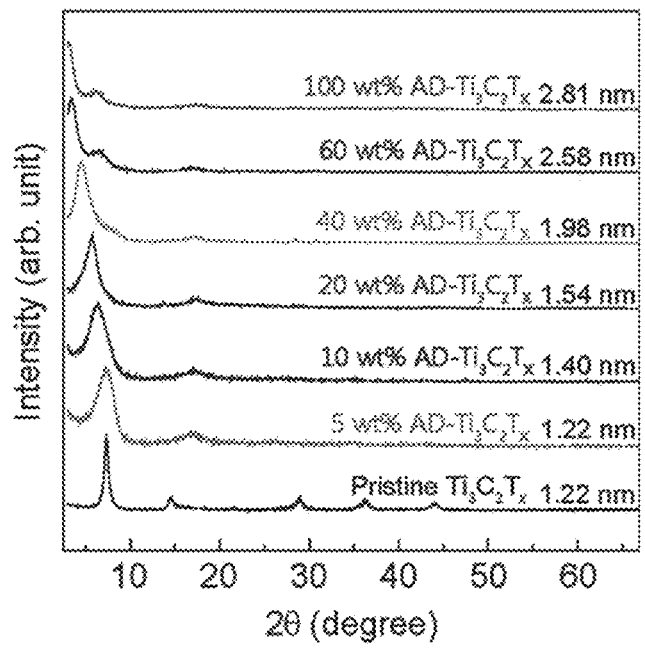
FIG. 9 is a graph illustrating the results of analysis of interlayer distance of the surface-modified two-dimensional MXene according to an embodiment of the present disclosure as a function of catechol derivative content, before and after surface modification, as determined by X-ray diffractometry (XRD).

As shown in FIG. 9, after analyzing the interlayer distance of the surface-modified two-dimensional MXene, a shift of (002) peak is observed, and it can be seen that the interlayer distance of MXene is increased in a range from 1.22 nm to 2.81 nm in proportion to the content of the catechol derivative. This is because the interlayer distance is increased, as the content of catechol derivative is increased. Therefore, this suggests that the surface of the two-dimensional MXene is satisfactorily modified with a catechol derivative.

Figure 10:
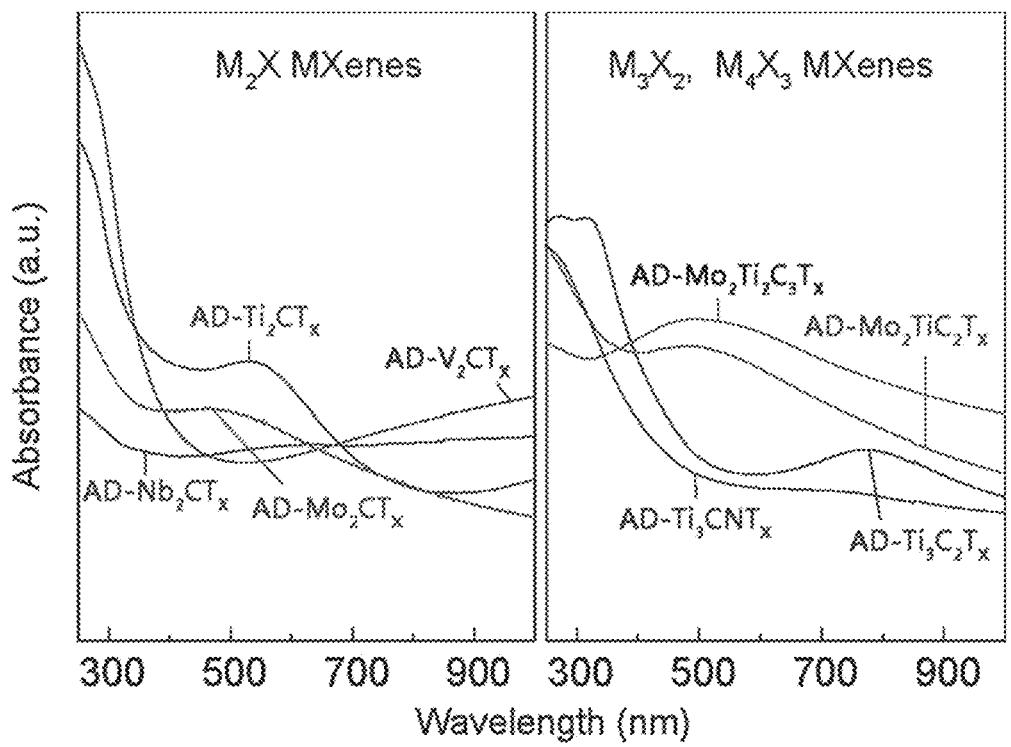
FIG. 10 shows graphs illustrating the outline of the UV peaks of the surface-modified two-dimensional MXene according to an embodiment of the present disclosure dispersed in ethanol, as analyzed by UV-Vis spectroscopy.

Test Example 5: Determination of Dispersion Stability of Surface-Modified Two-Dimensional MXene in Organic Solvent Through UV-VIS Spectroscopy The surface-modified two-dimensional MXene according to each of Example 1 (AD-$Ti_3C_2T_x$), Example 16 (AD-$Ti_3CNT_x$), Example 18 (AD-$Ti_2CT_x$), Example 20 (AD-$Mo_2Ti_2C_3T_x$), Example 22 (AD-$Nb_2CT_x$), Example 23 (AD-$V_2CT_x$), Example 24 (AD-$Mo_2CT_x$) and Example 25 (AD-$Mo_2TiC_2T_x$) was determined in terms of dispersion stability in ethanol by using UV-Vis spectroscopy, particularly by using UV JASCO V-670 spectrophotometer available from JASCO, in a wavelength range of 200-1000 nm. The results are shown in FIG. 10. It can be seen from the results of FIG. 10 that each MXene surface-modified with a hydrophobic catechol derivative according to each of Examples 1, 16, 18, 20 and 22-25 retains its original absorbance peaks. This suggests that the surface-modified MXene particles are dispersed stably in ethanol.

Test Example 6: Surface Analysis of Surface-Modified Two-Dimensional MXene Through XPS The surface-modified two-dimensional MXene (AD-MXene) according to Example 1 was subjected to surface analysis by using X-ray photoelectron spectroscopy (XPS) (Ulvac-PHI, Japan). The results are shown in FIG. 11.

Figure 11:
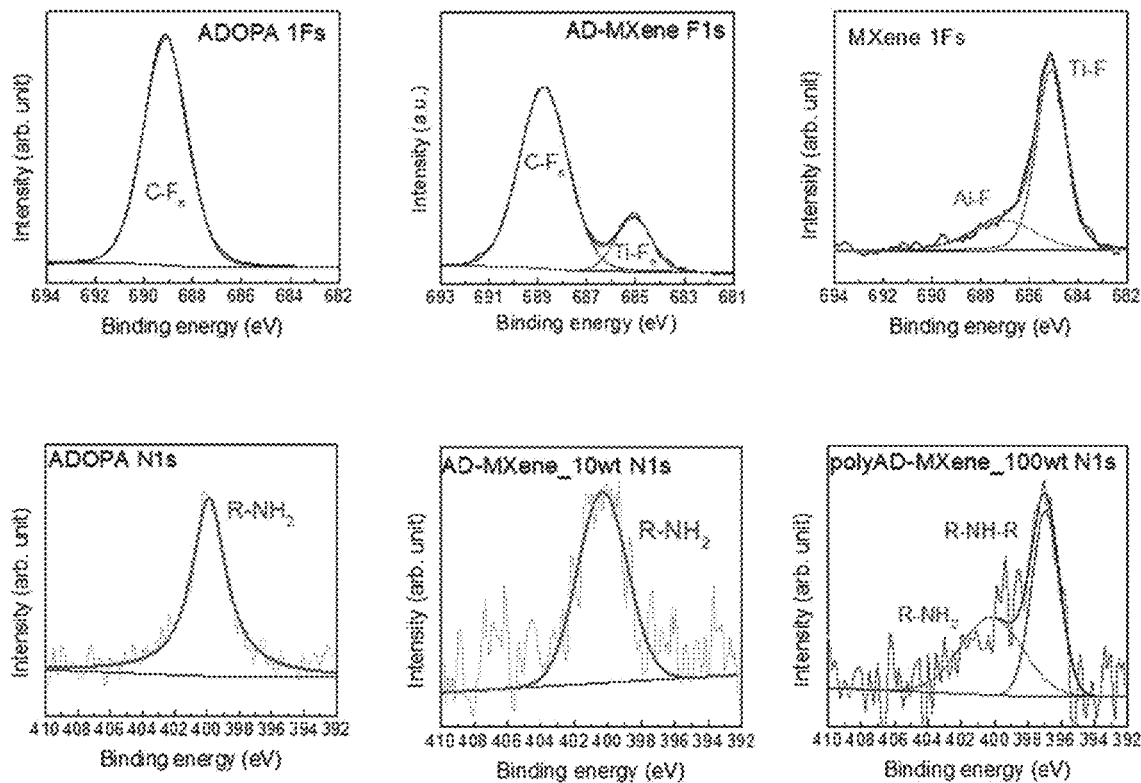
FIG. 11 shows the results of X-ray photoelectron spectroscopy of the surface-modified two-dimensional MXene according to an embodiment of the present disclosure, catechol or poly-catechol derivative used therefor, and a non-surface modified MXene.
Figure 11:
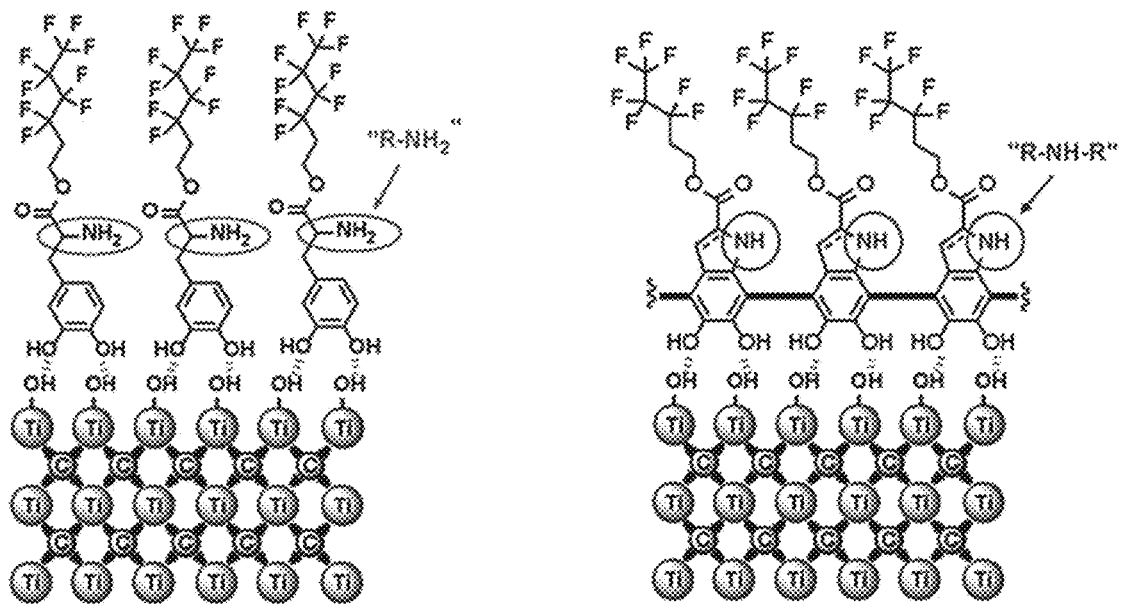

It can be seen from the F1$s$ peak graph of FIG. 11 that the MXene surface-modified with a catechol derivative shows not only the F1$s$ peak appearing in the MXene before surface modification but also the F1$s$ peak appearing in a catechol derivative (ADOPA). This suggests that the catechol derivative is adsorbed well to the hydroxy groups present on the surface of the MXene.

It can be also seen from the $N_1$ s peak graph of FIG. 11 that the MXene surface-modified with a catechol derivative (10 wt %) shows the peak of R—$NH_2$ present in a catechol single molecule (ADOPA).

In addition, when using a catechol derivative in a high concentration (100 wt %) as a surface functionalization reagent, the MXene surface-modified with the high concentration of ADOPA also shows the peak of R—NH—R present in a poly-catechol derivative (polyADOPA).

In other words, in case of the use 10 wt % ADOPA for the surface modification of the MXene, single ADOPA is adsorbed, whereas when 100 wt % ADOPA is used, self-polymerized polyADOPA is adsorbed on the MXene surface. This suggests that the surface-modified two-dimensional MXene is well adsorbed through the catechol or poly-catechol derivatives on the surface of the MXene.

Test Example 7: Comparison of Oxidation Stability Between Water-Dispersed MXene and Organic Solvent-Dispersed MXene The water-dispersed MXene ($Ti_3C_2T_x$_water) according to Comparative Example 1 and each organic solvent-dispersed MXene (AD-$Ti_3C_2T_x$_EtOH, AD-$Ti_3C_2T_x$_IPA) obtained through surface modification with a catechol derivative (ADOPA) represented by Chemical Formula 9 and dispersed in each of ethanol (EtOH) and isopropyl alcohol (IPA) were analyzed in terms of the oxidized state, after storing them in the air at room temperature for 30 days, by using UV-Vis spectroscopy. Particularly, the analysis was carried out by using UV JASCO V-670 spectrophotometer available from JASCO, wherein a change in peak intensity at 760 nm was followed in the results of UV-Vis spectroscopy of AD-$Ti_3C_2T_x$ MXene in Test Example 5 and FIG. 4. The results are shown in FIG. 12.

Figure 12:
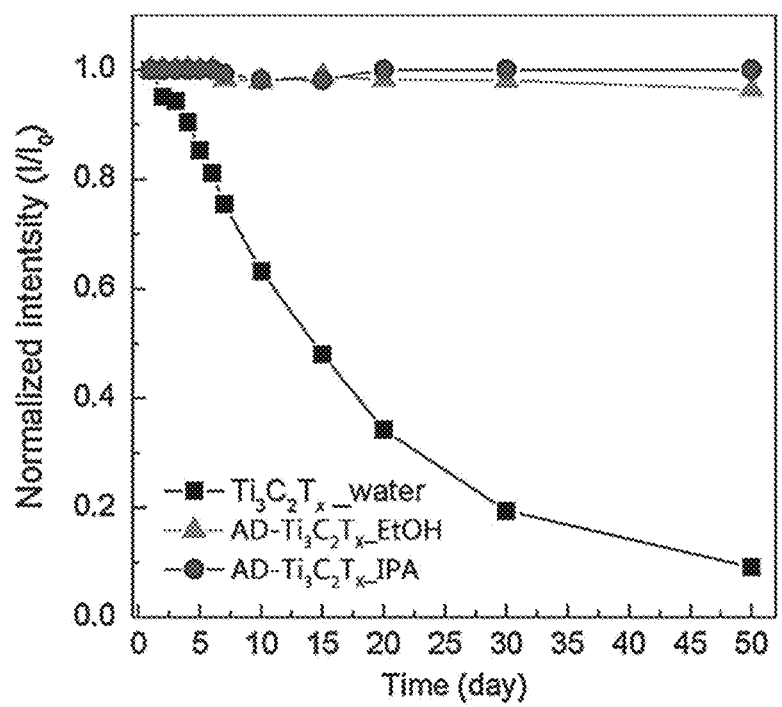
FIG. 12 is a graph illustrating the results of comparing the surface-modified two-dimensional MXene organic ink according to an embodiment of the present disclosure with a non-surface modified water-dispersed MXene solution in terms of oxidation stability.

As shown in FIG. 12, the water-dispersed MXene shows a significant decrease in initial absorbance at a wavelength of 760 nm with the lapse of time, which suggests that most of the water-dispersed MXene is oxidized. On the contrary, the surface-modified MXene according to Example 1 retains its initial absorbance at a wavelength of 760 nm, even after the lapse of 30 days, which suggests that substantially no oxidation occurs. It can be seen from the above results that the surface-modified and organic solvent-dispersed MXene according to an embodiment of the present disclosure shows higher oxidation stability as compared to the water-dispersed MXene, has excellent long-term storage stability, and thus can be used efficiently.

Figure 13:
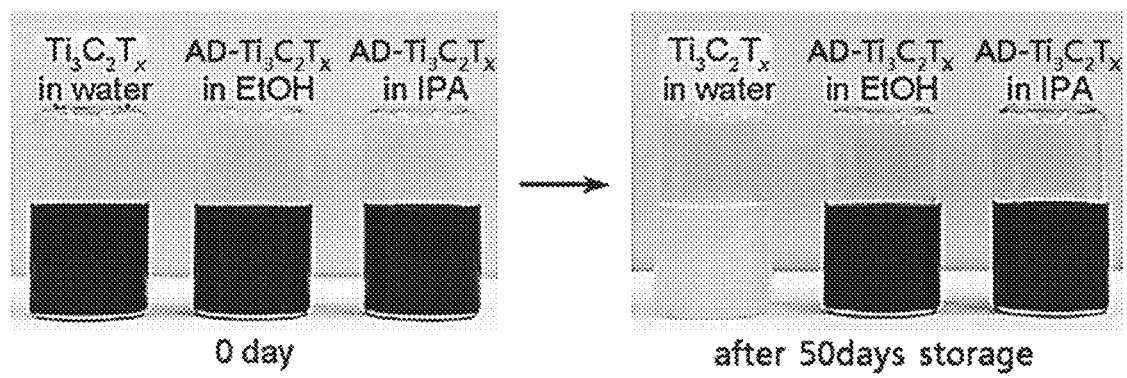
FIG. 13 shows the results of comparing the surface-modified two-dimensional MXene organic ink according to an embodiment of the present disclosure with a non-surface modified water-dispersed MXene solution in terms of oxidation stability.

Test Example 8: Comparison of Oxidation Stability Between Water-Dispersed MXene and Organic Solvent-Dispersed MXene by Naked Eyes The water-dispersed MXene ($Ti_3C_2T_x$ in water) according to Comparative Example 1 and each organic solvent-dispersed (AD-$Ti_3C_2T_x$ in EtOH, AD-$Ti_3C_2T_x$ in IPA) obtained through surface modification with a catechol derivative (ADOPA) represented by Chemical Formula 9 and dispersed in each of ethanol (EtOH) and isopropyl alcohol (IPA) were observed by the naked eyes for 50 days. The results are shown in FIG. 13. As shown in FIG. 13, after 50 days, the non-surface modified water-dispersed MXene is oxidized completely into $TiO_2$ and is converted into a milk-like white-colored liquid. On the contrary, the surface-modified MXene dispersed in each of ethanol and isopropyl alcohol is not oxidized but is present in the form of a black-colored solution. This suggests that the hydroxyl groups of MXene as a main cause of oxidation thereof are protected with the catechol derivative.

Figure 14:
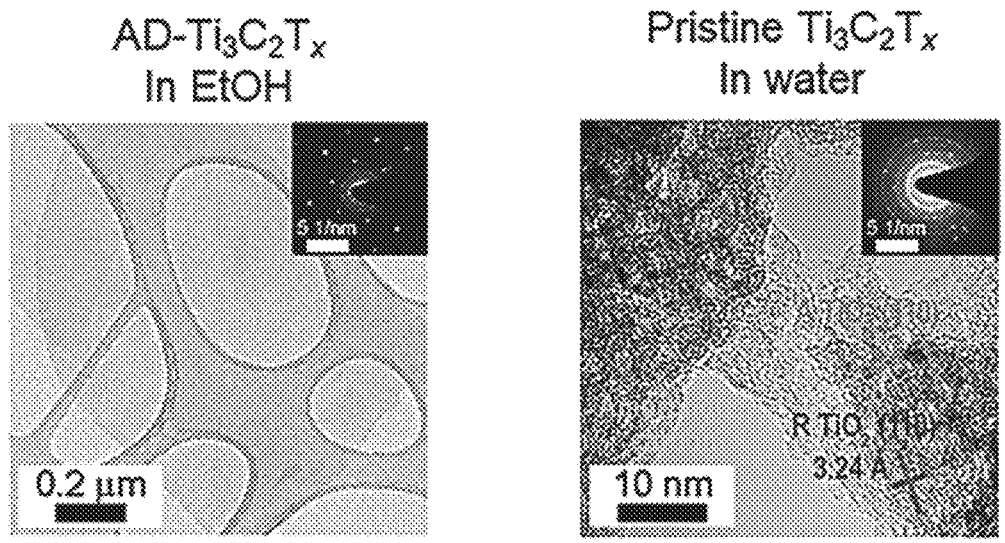
FIG. 14 shows the results of comparing the MXene sheets of the surface-modified two-dimensional MXene organic ink according to an embodiment of the present disclosure with those of a non-surface modified water-dispersed MXene solution, as observed through a transmission electron microscope.

Test Example 9: Microstructural Analysis of Surface-Modified Two-Dimensional MXene and Non-Surface Modified MXene Using TEM A transmission electron microscope (TEM) (alos F200X, FEI) was used to analyze the microstructure of the MXene (AD-$Ti_3C_2T_x$ in EtOH) surface-modified according to Example 1 and dispersed in ethanol and that of the non-surface modified MXene (Pristine-$Ti_3C_2T_x$ in Water) according to Comparative Example 1, after the lapse of 30 days. The results are shown in FIG. 14. As shown in FIG. 14, after 30 days, the surface-modified MXene retains the single layer like the original flake structure as it is. It can be predicted from the results that the two-dimensional MXene particles retain their unique properties even after surface modification. On the contrary, after 30 days, the non-surface modified MXene causes oxidation, and the original flake structure does not appear but growth of anatase and rutile nanocrystal $TiO_2$ is observed. It can be seen from the results that the MXene surface-modified with a catechol derivative shows significantly higher oxidation stability as compared to the non-surface modified water-dispersed MXene.

Test Example 10: Analysis of Surface Properties of Surface-Modified Two-Dimensional MXene Through Determination of Water Contact Angle A contact angle analyzer (GSS, Surface, Tech Co., Ltd., Korea) was used to determine the surface water contact angle of a bulk film obtained by using each of the water-dispersed MXene (Pristine-$Ti_3C_2T_x$n) according to Comparative Example 1 and the two-dimensional MXene surface-modified according to Example 1 and dispersed in isopropyl alcohol. The bulk film was obtained in the same manner as Test Example 2. The results are shown in FIG. 15.

Figure 15:
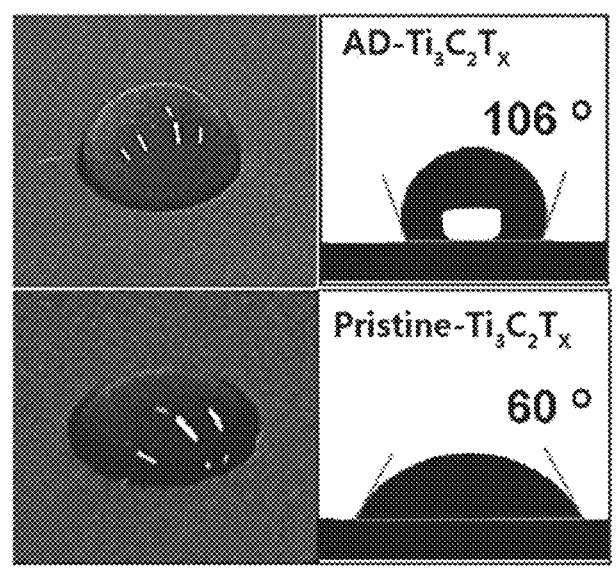
FIG. 15 shows the results of comparing the water contact angle of the surface-modified two-dimensional MXene organic ink according to an embodiment of the present disclosure with that of a film obtained by using a non-surface modified MXene.

As shown in FIG. 15, the surface-modified MXene film shows a contact angle of 106°, which suggests that it is significantly hydrophobitized as compared to the non-surface modified MXene film showing a contact angle of 60°. This suggests that the hydrophobic catechol derivative is satisfactorily adsorbed on the MXene surface.

Figure 16:
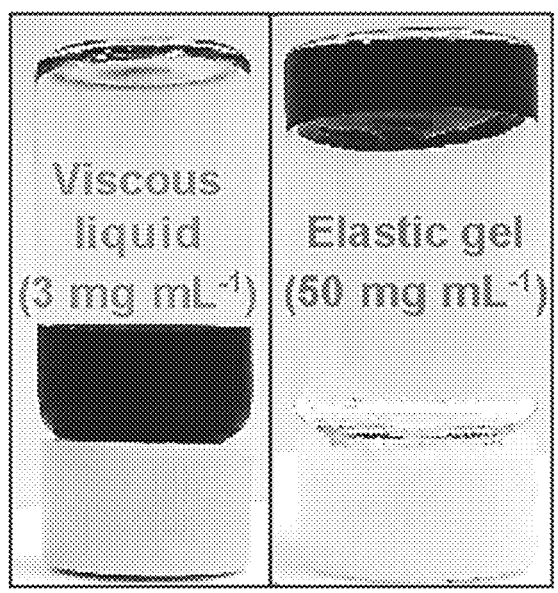
FIG. 16 shows behaviors of MXene organic ink depending on the concentration of the surface-modified two-dimensional MXene according to an embodiment of the present disclosure.

Test Example 11: Observation of Behaviors of Surface-Modified Two-Dimensional MXene Solution Depending on Concentration The viscoelasticity behaviors of the two-dimensional MXene solution surface-modified according to Example 1 and dispersed in ethanol were observed by the naked eyes. The results are shown in FIG. 16. At a low concentration of 3 mg/mL of MXene in ethanol, the solution shows a behavior like a complete viscous solution (left side of FIG. 16). On the other hand, when the MXene concentration is a high concentration of 50 mg/mL, the solution shows a behavior like an elastic gel, and the gel-like high-concentration MXene organic ink is still present on the bottom of a vial, even when the vial is upside down (right side of FIG. 16). This typically shows the properties of an elastic gel having liquid crystal characteristics, when the MXene can be dispersed stably at high concentration. It can be seen from the results that the two-dimensional MXene surface-modified with a catechol derivative is dispersed stably in an organic solvent at high concentration.

Figure 17:
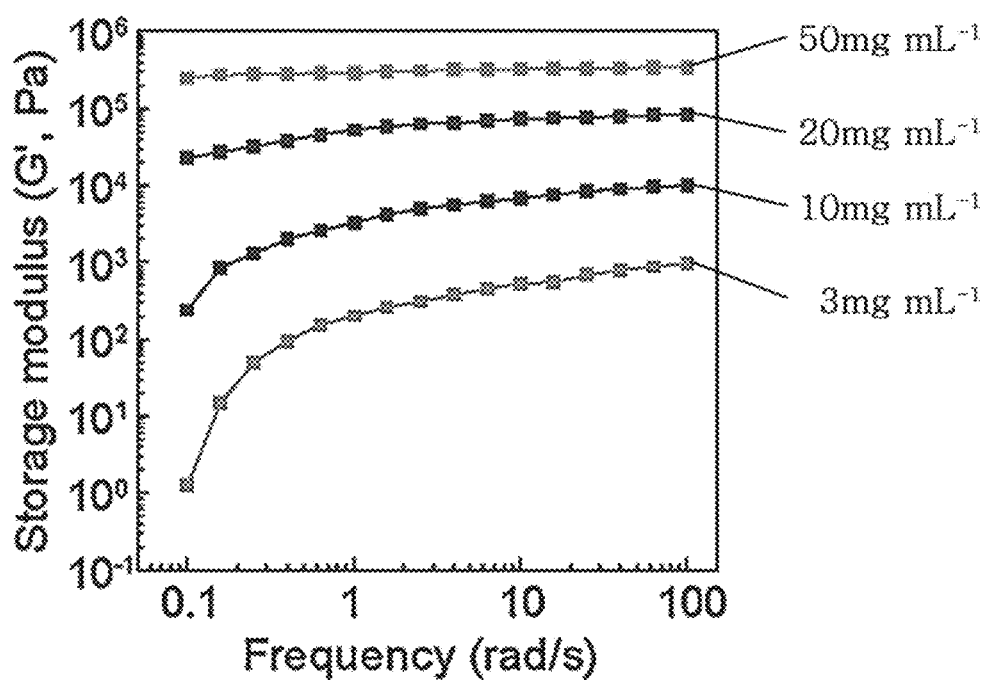
FIG. 17 is a graph illustrating storage modulus (G') of MXene organic ink depending on the concentration of the surface-modified two-dimensional MXene according to an embodiment of the present disclosure.

Test Example 12: Observation of Rheological Properties of Surface-Modified Two-Dimensional MXene Solution Through Rheometer A rheometer (MCR 302, Anton paar) was used to determine the rheological properties of the two-dimensional MXene solution surface-modified according to Example 1 and dispersed in acetonitrile depending on MXene concentration (3 mg/mL, 10 mg/mL, 20 mg/mL, 50 mg/mL). The results are shown in FIG. 17. As shown in FIG. 17, at a low concertation of 3 mg/mL or 10 mg/mL, the two-dimensional MXene solution shows a viscous fluid behavior in which storage modulus (G') varies with frequency. On the other hand, it can be seen that the MXene ink having a high concentration of 20 mg/mL or higher shows characteristics as an elastic gel, wherein storage modulus is constant regardless of frequency. This suggests that the high-concentration MXene ink shows nematic liquid crystal phases.

Test Example 13: Observation of Phase Change in High-Concentration Solution of Surface-Modified Two-Dimensional MXene Using Small Angle X-Ray Scattering (SAXS)

Figure 18:
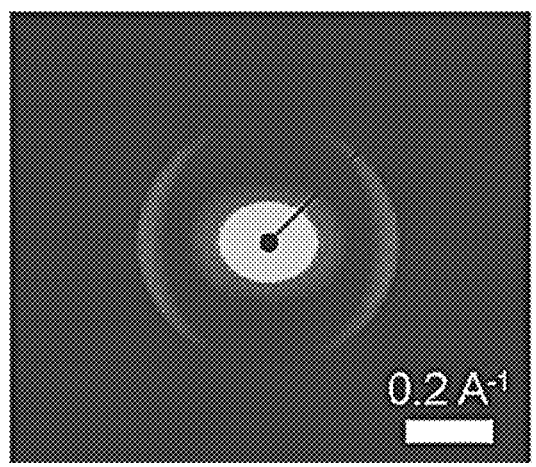
FIG. 18 shows the results of wide-angle X-ray scattering analysis of the surface-modified two-dimensional MXene according to an embodiment of the present disclosure in a high-concentration solution state.

Small Angle X-Ray Scattering (SAXS) was used to observe a phase change in the two-dimensional MXene solution surface-modified according to Example 1 and dispersed in ethanol at a high concentration of 50 mg/mL. Specifically, synchrotron small-angle X-ray scattering (SAXS) experiment was conducted at 4C beamline at the Pohang Accelerator Laboratory (PAL), Korea, with a X-ray wavelength of 0.7336 Å (16.9 keV). A two-dimensional charge-coupled detector (Mar USA, Inc.) was used. The results are shown in FIG. 18. As shown in FIG. 18, the MXene sheets in the high-concentration MXene solution are aligned in a fixed direction. This suggests that the high-concentration MXene ink solution shows clear orientational order, which is typical characteristics of nematic liquid crystals.

Preparation Example 2: Manufacture of Film Using MXene Organic Ink

Figure 19:
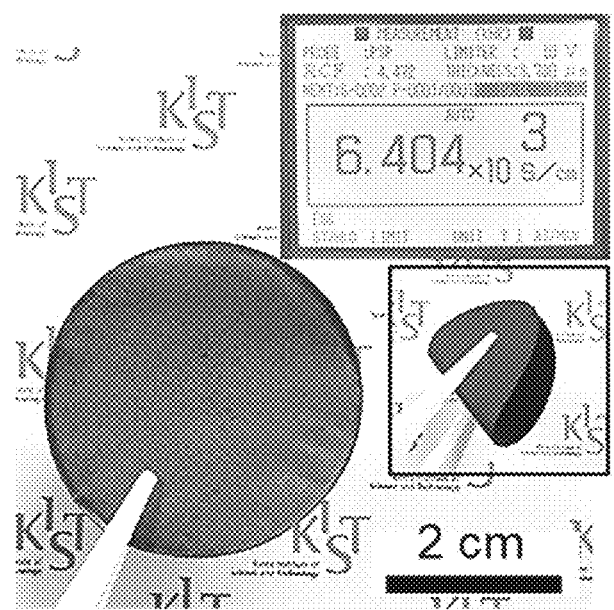
FIG. 19 shows a film obtained by using the MXene organic ink according to an embodiment of the present disclosure and the results of determination of electrical conductivity thereof.

The MXene ink solution surface-modified according to Example 1 and dispersed in ethanol was formed into a film through a vacuum filtration process using an anodic aluminum oxide film (pore size: 200 μm). As shown in FIG. 19, the resultant film shows flexibility and a high electrical conductivity of 6,404 S/cm. This suggests that the film retains an electrical conductivity at a level similar to the electrical conductivity of the water-dispersed pristine MXene without surface modification, even though the catechol derivative is adsorbed on the MXene surface for the purpose of hydrophobitization.

Preparation Example 3: Spray Coating Using MXene Organic Ink

Figure 20:
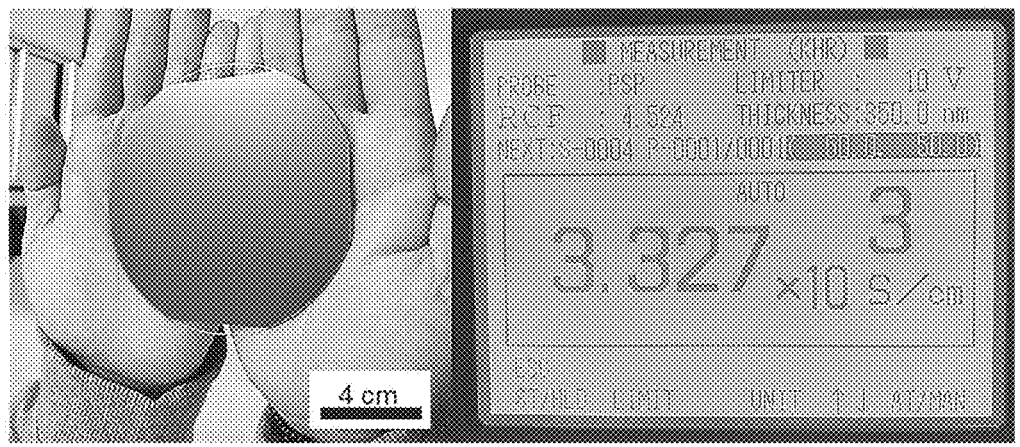
FIG. 20 shows the appearance of a spray coated material using the MXene organic ink according to an embodiment of the present disclosure and the results of determination of electrical conductivity thereof.

The MXene ink solution surface-modified according to Example 1 and dispersed in ethanol was used to carry out spray coating on glass wager (EAGLS-XG). As shown in the left side of FIG. 20, the ink is coated uniformly to a small thickness of 350 nm.

Test Example 14: Determination of Electrical Conductivity of Spray Coated Product Using MXene Organic Ink The electrical conductivity of the spray coated product according to Example 6 was determined in the same manner as Test Example 1. As shown in the right side of FIG. 20, the spray coated product shows a high electrical conductivity of 3,327 S/cm, which suggests that the film obtained according to Preparation Example 2 maintains its electrical conductivity even after spray coating.

Test Example 15: Comparison of Coatability Between Ethanol Dispersion of Two-Dimensional MXene Surface-Modified with Catechol Derivative and Non-Surface Modified Water-Dispersed MXene and Observation of Coatability by Naked Eyes The MXene solution (AD-$Ti_3C_2T_x$ (EtOH)) surface-modified with a catechol derivative according to Example 1 and dispersed in ethanol and the non-surface modified water-dispersed MXene solution (Pristine $Ti_3C_2T_x$ (Aqueous)) were coated on various types of substrates through dip coating. The results are shown in FIG. 21.

Figure 21:
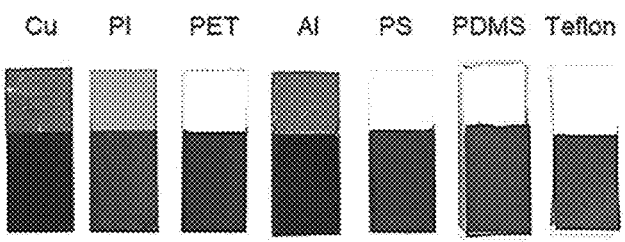
FIG. 21 shows the results of coating the surface-modified two-dimensional MXene organic ink according to an embodiment of the present disclosure and a non-surface modified water-dispersed MXene solution on various substrates.
Figure 21:
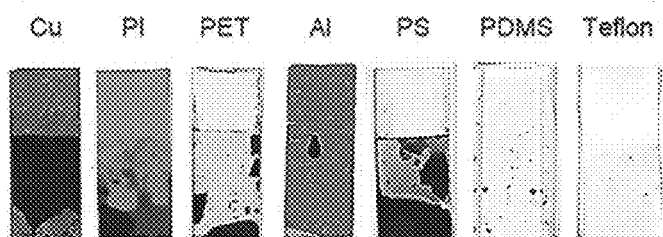

As shown in FIG. 21, the MXene solution surface-modified with a hydrophobic catechol derivative is coated uniformly and neatly on all of the copper (Cu), polyimide (PI), polyethylene terephthalate (PET), aluminum (Al), polystyrene (PS), polydimethyl siloxane (PDMS) and polytetrafluoroethylene (Teflon) substrates. On the other hand, the non-surface-modified hydrophilic water-dispersed MXene solution is not coated uniformly and neatly, and particularly, it is hardly coated on the PDMS and Teflon substrates. It can be predicted from the results that the MXene ink surface-modified with a hydrophobic catechol derivative can be used for coating on and composite formation with various types of polymers and substrates with ease.

Preparation Example 4: Polymer Composite Composition Using MXene Organic Ink and Manufacture of Film Using the Same To the MXene solution (MXene concentration 1 mg/mL) surface-modified with a catechol derivative according to Example 1 and dispersed in ethanol, 30 wt % of epoxy and urethane based on the total weight of the MXene solution was added. Then, the resultant mixture was agitated at room temperature (25° C.) for 1 hour to obtain MXene polymer composite composition. The resultant MXene polymer composite composition was formed into a film through a vacuum filtration process using an anodic aluminum oxide membrane (pore size: 200 μm). The resultant film shows flexibility. In addition, the electrical conductivity of the resultant film was determined in the same manner as Test Example 1. It can be seen that the film has an electrical conductivity of 100 S/cm. It can be predicted from the results that the surface-modified two-dimensional MXene solution has stable organic solvent-dispersed ink properties even after forming a polymer composite therewith, and thus can be used advantageously for manufacturing functional films including two-dimensional MXene particles and retaining the unique properties thereof, and for coating on various substrates through a liquid phase process, such as spray coating, spin coating, ink jet printing, or the like.

Figure 22:
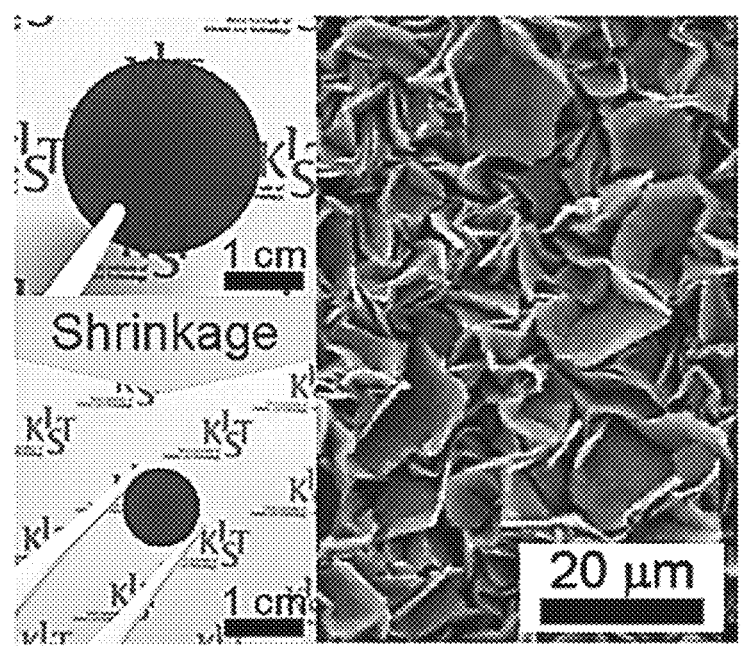
FIG. 22 shows the results of analysis of surface adhesion, after spin coating the surface-modified two-dimensional MXene organic ink according to an embodiment of the present disclosure on a polystyrene film.

Test Example 16: Test for Determining Adhesiveness of MXene Surface-Modified with Catechol Derivative, Spin-Coated on Thermally Deformable Polystyrene (PS) Film The MXene solution surface-modified with a catechol derivative according to Example 1 and dispersed in ethanol was spin-coated on a shrinkable polystyrene (PS) film, and the MXene-coated polystyrene film was heat treated on a hot plate at a temperature of 100° C. or 1 hour to test the adhesiveness of the surface-modified MXene with the polystyrene film. The results are shown in FIG. 22. As shown in FIG. 22, after carrying out the heat treatment for 1 hour, the MXene-coated polystyrene film is shrunk. After analyzing the coated film by using a scanning electron microscope (SEM) (Hitachi S4700, available from Hitachi), it can be seen that the MXene sheets retained the good adhesion to the polystyrene film, even after the polystyrene film is shrunk and wrinkled severely. This suggests that the hydrophobically surface-modified MXene organic ink has excellent coatability.

Preparation Example 5: Screen Printing Using MXene Organic Ink

Figure 23:
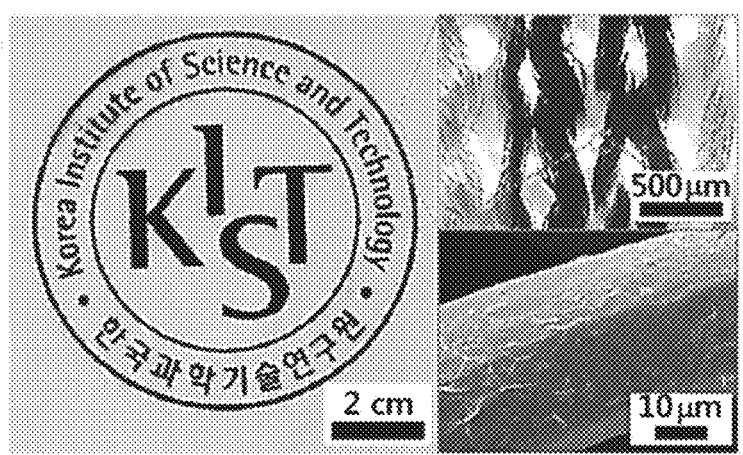
FIG. 23 shows the results of screen printing of the surface-modified two-dimensional MXene organic ink according to an embodiment of the present disclosure.

The MXene solution surface-modified with a catechol derivative according to Example 1 and dispersed in ethanol was screen printed on a fabric (cotton 100%). The results are shown in FIG. 23. As shown in FIG. 23, the MXene solution is neatly and clearly printed within a circle having a diameter of 8 cm. After observing the coated surface with an optical microscope (DM 2500 P, Leica), it can be seen that only the fiber strands present on the coated surface are coated with the MXene solution (the right upper side of FIG. 23). In addition, after observing the coated fiber strands with a scanning electron microscope (SEM) (Hitachi S4700, available from Hitachi), it can be seen that the fiber surfaces are uniformly and neatly coated with the two-dimensional MXene sheets. This suggests that the MXene organic ink surface-modified with a catechol derivative shows excellent coatability even on fine fibers having a diameter of 30-50 μm.

Figure 24:
FIG. 24 shows the results of a test for determining electrical conductivity of the surface-modified two-dimensional MXene high-concentration organic ink according to an embodiment of the present disclosure.

Preparation Example 6: Preparation of Electrically Conductive Paint Using MXene Organic Ink The MXene surface-modified with a catechol derivative according to Example 1 was dispersed in isopropyl alcohol at a high concentration of 50 mg/mL to obtain high-viscosity MXene ink, i.e. MXene paint. The resultant MXene paint is shown in FIG. 24. As shown in FIG. 24, the word, 'MXene' can be written with the MXene paint. It can be also seen that a bulb is lightened, since the MXene paint has electrical conductivity.

Test Example 17: Observation of Liquid Crystal Properties of MXene Ink Surface-Modified with Catechol Derivative Through Polarizing Optical Microscope (POM)

Figure 25:
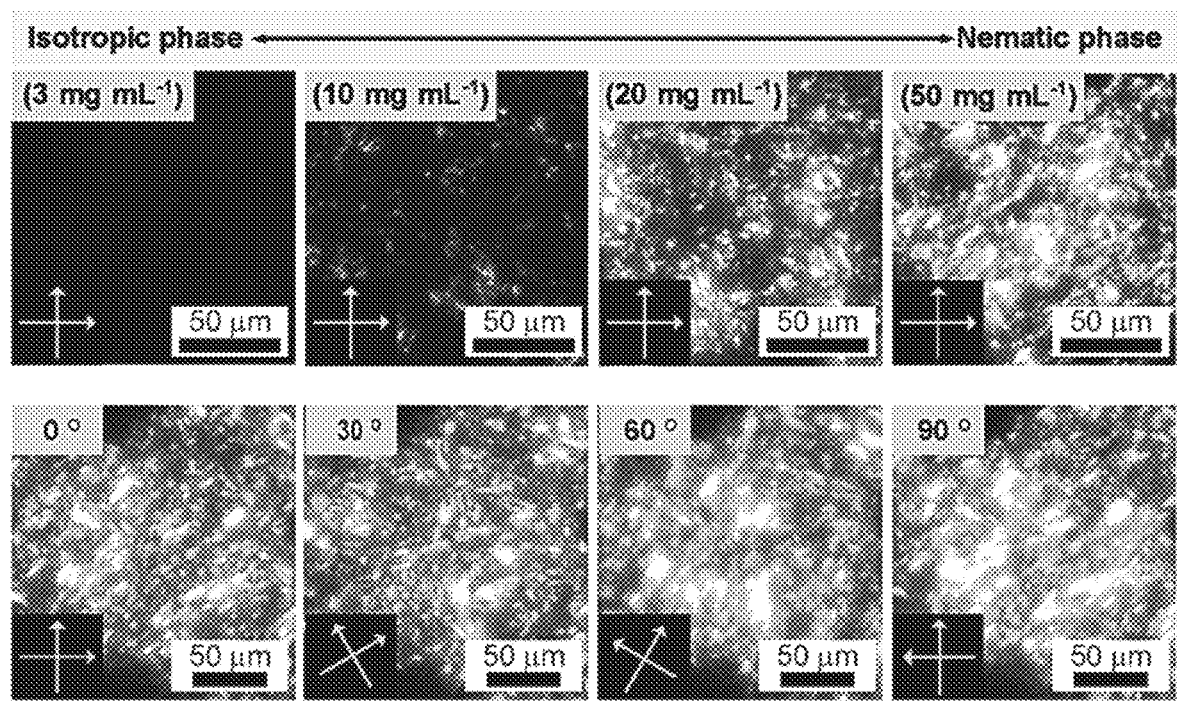
FIG. 25 shows the results of analysis of optical anisotropy of the surface-modified two-dimensional MXene organic ink according to an embodiment of the present disclosure as a function of concentration thereof.

The MXene solution surface-modified with a catechol derivative according to Example 1 and dispersed in acetonitrile (MeCN) was observed in terms of liquid crystal properties depending on MXene concentration (3 mg/mL, 10 mg/mL, 20 mg/mL, 50 mg/mL) of the MXene solution by using a polarizing optical microscope (POM: DM 2500 P, Leica). The results are shown in FIG. 25. As shown in FIG. 25, at a low concentration of 3 mg/mL, no liquid crystal properties can be observed. On the other hand, at a concentration of 20 mg/mL or higher, liquid crystal properties can be observed clearly. In addition, it can be seen that when the sample stage is rotated at 0°, 30°, 60° and 90° in the case of the ink having a high concentration of 50 mg/mL, the MXene particles shine brightly. This shows the properties appearing when the MXene sheets are dispersed well in a specific solvent at high concentration and aligned in a fixed direction. It can be seen that the MXene organic ink having a high concentration of 20 mg/mL or higher shows nematic liquid crystal properties.

Test Example 18: Observation of Liquid Crystal Properties of MXene Ink Surface-Modified with Catechol Derivative Depending on Organic Solvent Through Polarizing Optical Microscope (POM)

Figure 26:
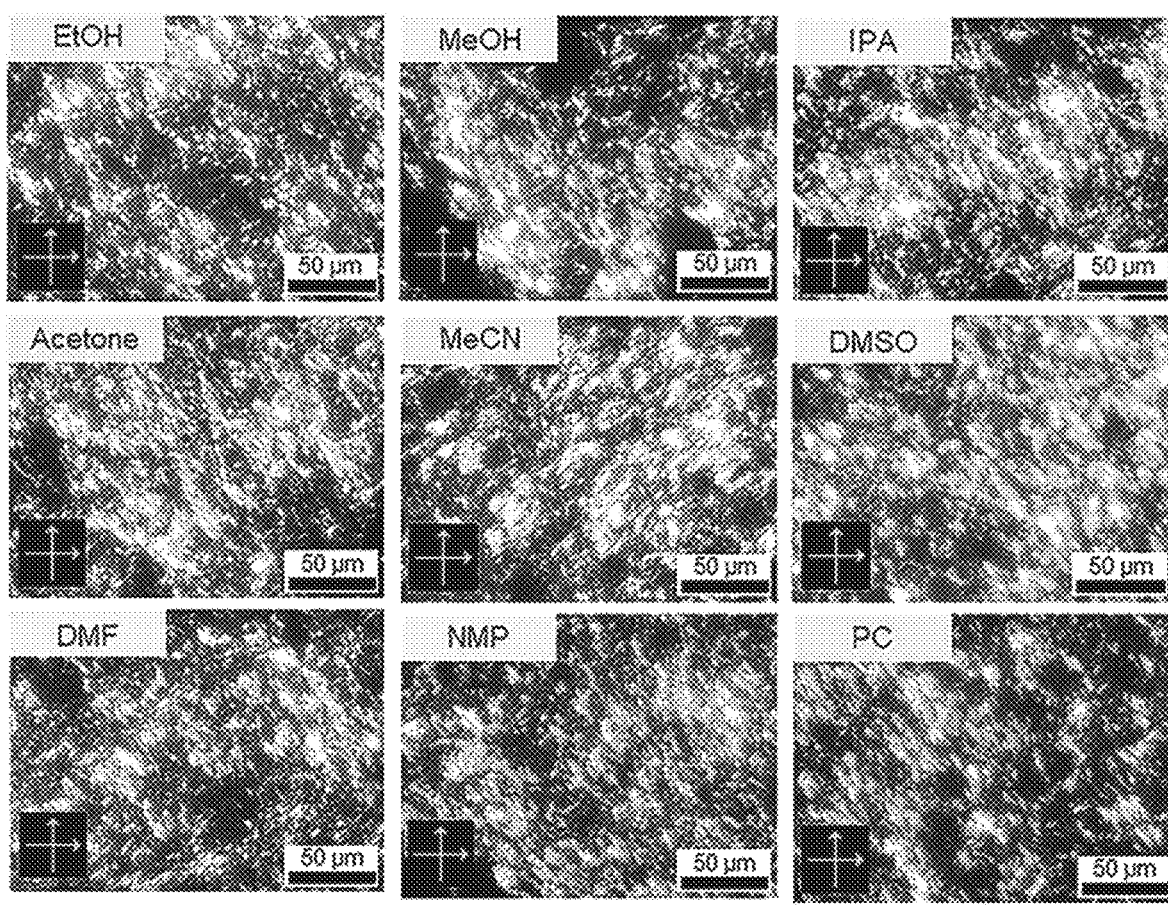
FIG. 26 shows liquid crystal phase behaviors of the surface-modified two-dimensional MXene organic ink according to an embodiment of the present disclosure dispersed in various organic solvents.

The MXene solution (MXene concentration: 50 mg/mL) surface-modified with a catechol derivative according to Example 1 and dispersed in each of ethanol (EtOH), methanol (MeOH), isopropyl alcohol (IPA), acetone, acetonitrile (MeCN), dimethyl sulfoxide (DMS), dimethyl formamide (DMF), N-methyl-2-pyrrolidone (NMP) and propylene carbonate (PC) was observed in terms of liquid crystal properties by using a polarizing optical microscope (POM: DM 2500 P, Leica). The results are shown in FIG. 26. As shown in FIG. 26, brightly shining liquid crystal properties are observed in all of the nine types of organic solvents. This suggests that the MXene surface-modified with a catechol derivative can be dispersed stably in various organic solvents, and shows liquid crystal properties, when being dispersed at high concentration.

Test Example 19: Observation of Liquid Crystal Properties of Various Types of MXene Ink Surface-Modified with Catechol Derivative and Dispersed in Ethanol Through Polarizing Optical Microscope (POM)

Figure 27:
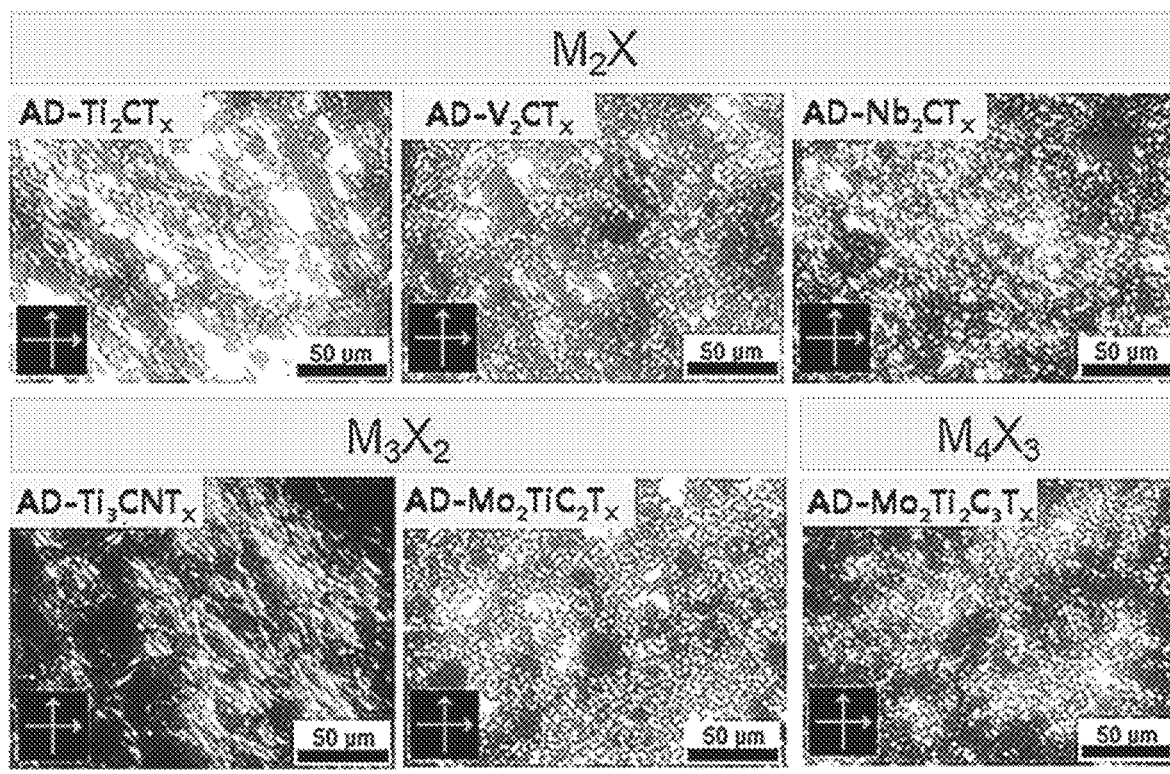
FIG. 27 shows liquid crystal phase behaviors of the surface-modified two-dimensional MXene organic ink according to an embodiment of the present disclosure dispersed in ethanol.

The MXene solution (MXene concentration: 50 mg/mL) prepared by dispersing the MXene obtained according to each of Example 16 (AD-Ti$_3$CNT$_x$), Example 18 (AD-Ti$_2$CT$_x$), Example 20 (AD-Mo$_2$Ti$_2$C$_3$T$_x$) Example 22 (AD-Nb$_2$CT$_x$), Example 23 (AD-V$_2$CT$_x$) and Example 25 (AD-Mo$_2$TiC$_2$T$_x$) in ethanol was observed in terms of liquid crystal properties by using a polarizing optical microscope (POM: DM 2500 P, Leica). The results are shown in FIG. 27. As shown in FIG. 27, each binary MXene (Ti$_2$C, Nb$_2$C, V$_2$C), each ternary MXene (Ti$_3$CN, Mo$_2$TiC$_2$) and the quaternary MXene (Mo$_2$Ti$_2$C$_3$), surface-modified with a catechol derivative, show liquid crystal properties. It can be seen that the binary MXene, ternary MXene and the quaternary MXene other than Ti$_3$C$_2$ according to Example 1 show excellent dispersibility and realize liquid crystal properties through surface modification with a catechol derivative, when being dispersed at high concentration.

Test Example 20: Observation of Liquid Crystal Properties of MXene-Polymer Composite Ink Through Polarizing Optical Microscope (POM) after Forming Composite Between Polymer and MXene Surface-Modified with Catechol Derivative and Dispersed in Acetone The MXene solution prepared by dispersing 50 mg of the MXene surface-modified with a catechol derivative according to Example 1 in 50 mL of acetone was mixed with each of a polyvinylidene fluoride-co-hexafluoropropylene (PVDF-HFP) solution prepared by dispersing 50 mg of PVDF-HFP in 10 mL of acetone and a polystyrene (PS) solution prepared by dispersing 50 mg of PS in 10 mL of acetone, and the resultant mixture was agitated for 30 minutes and subjected to centrifugal separation to obtain MXene-polymer composite ink (AD-Ti$_3$C$_2$T$_x$@PVDF-HFP and AD-Ti$_3$C$_2$T$_x$@PS) having a high concentration (50 mg/mL). The liquid crystal properties of each ink were observed through a polarizing optical microscope (POM: DM 2500 P, Leica).

Figure 28:
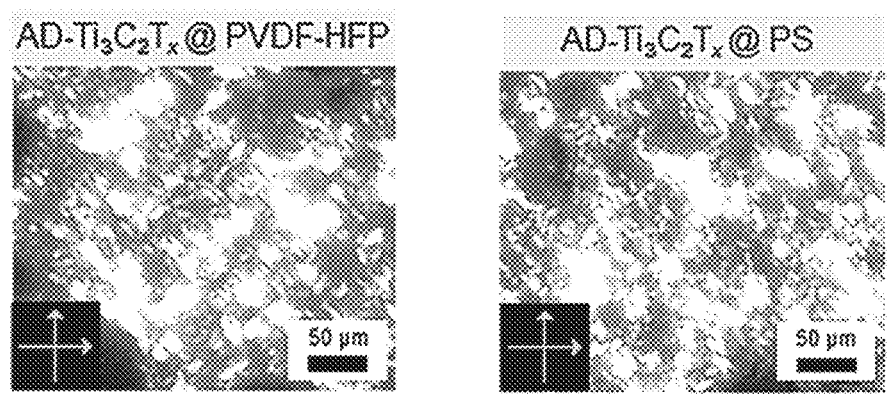
FIG. 28 shows liquid crystal phase behaviors of the MXene-polymer composite formed between the surface-modified two-dimensional MXene organic ink according to an embodiment of the present disclosure and each of polyvinylidene fluoride-co-hexafluoropropylene (PVDF-HFP) and polystyrene (PS) polymers, dispersed in acetone.

The results are shown in FIG. 28. As shown in FIG. 28, even when forming a composite of the high-concentration MXene solution including the surface-modified MXene according to the present disclosure with a polymer, the composite shows liquid crystal properties.

What is claimed is:

1. A two-dimensional MXene surface-modified with a catechol derivative wherein the catechol derivative is present as a monomer and does not include a poly-catechol derivative.

2. The surface-modified two-dimensional MXene according to claim 1, wherein the catechol derivative comprises a polyphenol moiety in the form of a phenyl group containing 2 to 5 hydroxyl (—OH) groups.

3. The surface-modified two-dimensional MXene according to claim 1, wherein the catechol derivative is represented by any one of the following Chemical Formula 1 to Chemical Formula 8:

[Chemical Formula 1]

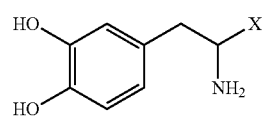

-continued

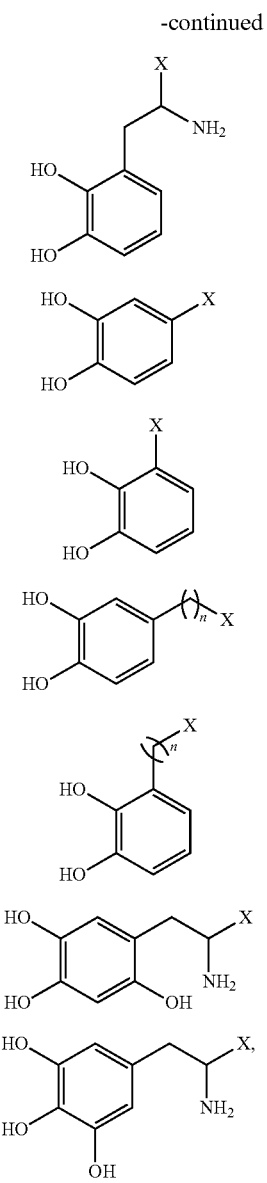

[Chemical Formula 2]

[Chemical Formula 3]

[Chemical Formula 4]

[Chemical Formula 5]

[Chemical Formula 6]

[Chemical Formula 7]

[Chemical Formula 8]

wherein, X is selected from a hydrogen atom (—H), ester group (—COOR), amide group (—CONHR), thioester group (—COSR), hydrocarbon group (—R) and an ether group (—R—O—R'—), each of R and R' is independently selected from $C_1$-$C_{25}$ aliphatic hydrocarbons and aromatic hydrocarbons, and n is an integer of 1-10.

4. The surface-modified two-dimensional MXene according to claim 3, wherein each of R and R' independently represents: a saturated or unsaturated cyclic or chain-like hydrocarbon selected from $C_1$-$C_{25}$ alkyl, $C_2$-$C_{25}$ alkenyl, $C_2$-$C_{25}$ alkynyl and $C_6$-$C_{25}$ aryl groups; or a saturated or unsaturated heterocyclic hydrocarbon containing 1-25 carbon atoms and at least one heteroatom selected from nitrogen, oxygen and sulfur.

5. The surface-modified two-dimensional MXene according to claim 4, wherein the saturated or unsaturated chain-like hydrocarbon comprises at least one selected from nitrogen, oxygen, sulfur, sulfinyl and sulfonyl, in the middle of said saturated or unsaturated chain-like hydrocarbon or at a side chain thereof.

6. The surface-modified two-dimensional MXene according to claim 4, wherein each of the cyclic or chain-like hydrocarbon and heterocyclic hydrocarbon is not substituted, or is independently substituted with at least one substituent selected from a $C_1$-$C_5$ alkyl group, $C_6$-$C_{25}$ aryl group, fluorine, chlorine, bromine and iodine.

7. The surface-modified two-dimensional MXene according to claim 4, wherein each of R and R' independently represents a saturated or unsaturated cyclic or chain-like hydrocarbon selected from $C_1$-$C_{13}$ alkyl, $C_2$-$C_{13}$ alkenyl, $C_2$-$C_{13}$ alkynyl and $C_6$-$C_{10}$ aryl groups, and each hydrocarbon is independently substituted with at least one substituent selected from a $C_1$-$C_5$ alkyl group, $C_6$-$C_{10}$ aryl group, fluorine, chlorine, bromine and iodine.

8. The surface-modified two-dimensional MXene according to claim 1, wherein the two-dimensional MXene to be surface-modified comprises at least one layer with a two-dimensional array of crystal cells represented by the empirical formula of $M_{n+1}X_n$, each X is positioned in an octahedral array formed of a plurality of M elements, M is at least one metal selected from the group consisting of Group IIIB metals, Group IVB metals, Group VB metals and Group VIB metals, each X represents C, N or a combination thereof, and n is 1, 2, 3 or 4.

9. The surface-modified two-dimensional MXene according to claim 1, wherein the two-dimensional MXene to be surface-modified comprises at least one layer with a two-dimensional array of crystal cells represented by the empirical formula of $M'_2M''_nX_{n+1}$, each X is positioned in an octahedral array formed of a plurality of M' and M" elements, M' and M" are different from each other, and each of M' and M" is at least one metal selected from the group consisting of Group IIIB metals, Group IVB metals, Group VB metals and Group VIB metals, each X represents C, N or a combination thereof, and n is 1 or 2.

10. A method for preparing the two-dimensional MXene surface-modified with a catechol derivative as defined in claim 1, including the steps of:

(1) preparing an aqueous MXene solution including a two-dimensional MXene dispersed therein through an acid etching process; and (2) mixing and agitating the aqueous MXene solution obtained from step (1) with an organic solution including a catechol derivative dispersed in an organic solvent so that the two-dimensional MXene is surface-modified with the catechol derivative.

11. MXene organic ink comprising the two-dimensional MXene surface-modified with a catechol derivative as defined in claim 1, wherein the surface-modified MXene is dispersed in an organic solvent.

12. The MXene organic ink according to claim 11, wherein the surface-modified two-dimensional MXene is dispersed in the organic solvent at a concentration of 20 mg/mL or higher.

13. The MXene organic ink according to claim 11, which shows liquid crystal properties.

14. An electrically conductive film comprising the MXene organic ink as defined in claim 11.

15. An electrically conductive flexible electrode comprising the MXene organic ink as defined in claim 11.

16. An electrically conductive polymer composite comprising the MXene organic ink as defined in claim 11.

\* \* \* \* \*